(12) United States Patent
Hunt et al.

(10) Patent No.: US 8,034,913 B2
(45) Date of Patent: Oct. 11, 2011

(54) RECOMBINANTLY MODIFIED PLASMIN

(75) Inventors: Jennifer A. Hunt, Raleigh, NC (US); Valery Novokhatny, Raleigh, NC (US)

(73) Assignee: Grifols Therapeutics Inc., Research Triangle Park, NC (US)

( * ) Notice: Subject to any disclaimer, the term of this patent is extended or adjusted under 35 U.S.C. 154(b) by 854 days.

(21) Appl. No.: 11/568,023

(22) PCT Filed: Apr. 21, 2005

(86) PCT No.: PCT/US2005/013562
§ 371 (c)(1),
(2), (4) Date: Feb. 1, 2008

(87) PCT Pub. No.: WO2005/105990
PCT Pub. Date: Nov. 10, 2005

(65) Prior Publication Data
US 2010/0304465 A1 Dec. 2, 2010

Related U.S. Application Data

(60) Provisional application No. 60/564,472, filed on Apr. 22, 2004.

(51) Int. Cl.
*C07H 21/04* (2006.01)
*C12N 15/63* (2006.01)
*A61K 31/70* (2006.01)

(52) U.S. Cl. .................. 536/23.2; 536/23.4; 435/320.1; 435/455

(58) Field of Classification Search ........................ None
See application file for complete search history.

(56) References Cited

U.S. PATENT DOCUMENTS

| | | | |
|---|---|---|---|
| 4,631,211 A | 12/1986 | Houghten et al. | |
| 4,652,639 A | 3/1987 | Stabinsky | |
| 4,774,087 A | 9/1988 | Wu | |
| 5,149,533 A * | 9/1992 | Mulvihill et al. | 424/94.64 |
| 6,218,517 B1 | 4/2001 | Suzuki | |
| 6,312,893 B1 | 11/2001 | Van Ness | |
| 6,355,243 B1 | 3/2002 | Novokhatny | |
| 6,444,422 B2 | 9/2002 | Van Ness | |
| 6,538,103 B1 | 3/2003 | Ji et al. | |
| 6,613,508 B1 | 9/2003 | Van Ness | |
| 6,623,928 B2 | 9/2003 | Van Ness | |
| 6,664,112 B2 | 12/2003 | Mulligan | |
| 6,946,438 B1 | 9/2005 | Nagai et al. | |
| 7,253,264 B1 | 8/2007 | Lauffer et al. | |
| 2003/0012778 A1 | 1/2003 | Zimmerman | |
| 2003/0026798 A1 | 2/2003 | Zimmerman | |
| 2003/0147877 A1 | 8/2003 | Trese et al. | |
| 2003/0175264 A1 | 9/2003 | Jesmok | |
| 2005/0118158 A1 | 6/2005 | Pakola et al. | |
| 2005/0124036 A1 | 6/2005 | Susilo | |

FOREIGN PATENT DOCUMENTS

| | | |
|---|---|---|
| CA | 2045869 | 12/1991 |
| WO | WO 97/27331 A2 | 7/1997 |
| WO | WO 99/05322 A1 | 2/1999 |
| WO | WO 01/94366 A1 | 12/2001 |
| WO | WO 02/50290 A1 | 6/2002 |
| WO | WO 03/054232 A2 | 7/2003 |
| WO | WO 2004/052228 A2 | 6/2004 |
| WO | WO 2005/105990 | 11/2005 |
| WO | WO 2007/047874 | 4/2007 |
| WO | WO 2009/073471 | 6/2009 |

OTHER PUBLICATIONS

Hunt et al. Simplified recombinant plasmin: Production and functional comparison of a novel thrombolytic molecule with plasma-derived plasmin. Thromb. Haemost 100:413-419, 2008.*
Andrianov, S.I., et al., "Peculiarities of Hydrolytic Action of Plasmin, Miniplasmin, Microplasmin and Trypsin on Polymeric Fibrin," *Ukr. Biokhim. Zh.*, 64(3): 14-20 (1992).
Anonick, P., et al., "Regulation of Plasmin, Miniplasmin and Streptokinase—Plasmin Complex by—$\alpha_2$-Antiplasmin, $\alpha_2$-Macroglobulin, and Antithrombin III in the Presence of Heparin," *Thrombosis Res.*, 59: 449-462 (1990).
Bennett, D., et al., "Kinetic Characterization of the Interaction of Biotinylated Human Interleukin 5 with an Fc Chimera of its Receptor $\alpha$ Subunit and Development of an ELISA Screening Assay using Real-Time Interaction Biosensor Analysis," *J. Molecular Recognition*, 8: 52-58 (1995).
Bowie, J.U., et al., "Deciphering the Message in Protein Sequences: Tolerance to Amino Acid Substitutions," *Science*, 247: 1306-1310 (1990).
Burck, P.J., et al., "Characterization of a Modified Human Tissue Plasminogen Activator Comprising a Kringle-2 and a Protease Domain, " *J Biol. Chem.*, 265(9): 5170-5177 (1990).
Cao, Y., et al., "Kringle Domains of Human Angiostatin," *J. Biol. Chem.*, 271(46): 29461-29467 (1996).
Castellino, F.J., and S.G. McCance, "The kringle domains of human plasminogen," *Ciba Found. Symp.*, 212: 46-65 (1997).
Chang, Y., et al., "Structure and Ligand Binding Determinants of the Recombinant Kringle 5 Domain of Human Plasminogen," *Biochemistry*, 37: 3258-3271 (1998).
Chase, T. and E. Shaw, "Titration of Trypsin, Plasmin, and Thrombin with p-Nitrophenyl p-Guanidinobenzoate HCl," *Methods Enzymol.*, 19: 20-27 (1970).
Cunningham, B.C., and J.A. Wells, "High-Resolution Epitope Mapping of hGH-Receptor Interactions by Alanine-Scanning Mutagenesis," *Science*, 244: 1081-1085 (1989).
de Vos, A.M., et al., "Human *Growth Hormone and Extracellular Domain of Its Receptor: Crystal Structure of the Complex*," *Science*, 255: 306-312 (1992).
Douglas, J.T., et al., "The Two-Domain NK1 Fragment of Plasminogen: Flding, Ligand Binding, and Thermal Stability Profile," *Biochemistry*, 41(10): 3302-3310 (2002).
Goretzki, L., et al., "Binding of the NG2 Proteoglycan to Kringle Domains Modulates the Functional Properties of Angiostatin and Plasmin (ogen)," *J. Biol. Chem.*, 275(37): 28625-28633 (2000).

(Continued)

*Primary Examiner* — Quang Nguyen
(74) *Attorney, Agent, or Firm* — Womble Carlyle Sandridge & Rice, PLLC

(57) ABSTRACT

Polynucleotides and polypeptides relating to a recombinantly-modified plasmin(ogen) molecule are provided. The plasmin(ogen) molecule has a single kringle domain N-terminal to the activation site present in the native human plasminogen molecule, and exhibits lysine-binding and significant enzymatic characteristics associated with the native enzyme.

10 Claims, 7 Drawing Sheets

OTHER PUBLICATIONS

Gribskov, M., and Richard R. Burgess, "Sigma factors from *E. coli, B. subtilis*, phage SP01, and phage T4 are homologous proteins," *Nucl. Acids Res.*, 14(6): 6745-6763 (1986).

Hoover, G.J., et al., "Amino Acids of the Recombinant Kringle 1 Domain of Human Plasminogen that Stabilize Its Interaction with ω-Amino Acids," *Biochemistry*, 32(41): 10936-10943 (1993).

Houghten, R.A., "General method for the rapid solid-phase synthesis of large numbers of peptides: Specificity of antigen-antibody interaction at the level of individual amino acids," *Proc. Natl. Acad. Sci. USA*, 82: 5131-5135 (1985).

Johanson, K., et al., "Binding Interactions of Human Interleukin 5 with Its Receptor α Subunit," *J. Biol. Chem.*, 270(16): 9459-9471 (1995).

Kolev, K., et al., "Functional Evaluation of the Structural Features of Proteases and Their Substrate in Fibrin Surface De tradation," *J. Biol. Chem.*, 272(21): 13666-75 (1997).

Komorowicz, E., et al., "Fibrinolysis with Des-Kringle Derivatives of Plasmin and Its Modulation by Plasma Protease Inhibitors," *Biochemistry*, 37(25): 9112-9118 (1998).

Lee, H., et al., "Disruption of Interkringle Disulfide Bond of Plasminogen Kringle 1-3 Changes the Lysine Binding Capability of Kringle 2, But Not Its Antiangiogenic Activity," *Arch. Biochem. Biophys.*, 375(2): 359-363 (2000).

Lerch, P.G., et al., "Localization of Individual Lysine-Binding Regions in Human Plasminogen and Investigations on Their Complex-Forming Properties," *Eur. J. Biochem.*, 107(1): 7-13 (1980).

Lin, L-F., et al., "Epsilon Amino Caproic Acid Inhibits Streptokinase—Plasminogen Activator Complex Formation and Substrate Binding through Kringle-Dependent Mechanisms," *Biochemistry*, 39: 4740-4745 (2000).

Lucas, M.A., et al., "The Binding of Human Plasminogen to Fibrin and Fibrinogen," *J. Biol. Chem.*, 258(7): 4249-4256 (1983).

Marder, V.J., et al., "Plasmin Induces Local Thrombolysis without Causing Hemorrhage: A Comparison with Tissue Plasminogen Activator in the Rabbit," *Thromb. Haemost.*, 86(3): 739-745 (2001).

Matsuka, Y.V., et al., "Fluorescence spectroscopic analysis of ligand binding to kringle 1+2+3 and kringle 1 fragments from human plasminogen," *Eur. J. Biochem.*, 190: 93-97 (1990).

McCance, S., et al., "Amino Acid Residues of the Kringle-4 and Kringle-5 Domains of Human Plasminogen that Stabilize their Interactions with ω-Amino Acid Ligands," *J. Biol. Chem.*, 269(51): 32405-32410 (1994).

Menhart, N., et al., "Functional Independence of the Kringle 4 and Kringle 5 Regions of Human Plasminogen," *Biochemistry*, 32: 8799-8806 (1993).

Motta, A., et al., "Complete Assignment of the Aromatic Proton Magnetic Resonance Spectrum of the Kringle 1 Domain from Human Plasminogen: Structure of the Ligand-Binding Site," *Biochemistry*, 26(13): 3827-3836 (1987).

Novokhatny, V., et al., "Thrombolytic potency of acid-stabilized plasmin: superiority over tissue-type plasminogen activator in an in vitro model of catheter-assisted thrombolysis," *J. Thromb. Haemost.*, 1(5): 1034-1041 (2003).

Novokhatny, V., and Stanislav A. Kudinov, "Domains in Human Plasminogen," *J. Mol. Biol.*, 179: 215-232 (1984).

Novokhatny, V., et al., "Analysis of Ligand Binding to Kringles 4 and 5 Fragments from Human Plasminogen," *Thromb Res.*, 53(3): 243-52 (1989).

Powell, J.R., and Francis J. Castellino, "Activation of Human Neo-Plasminogen-Val$_{442}$ by Urokinase and Streptokinase and a Kinetic Characterization of Neo-Plasmin-Val$_{442}$," *J. Biol. Chem.*, 255(11): 5329-5335 (1990).

Rejante, M.R. and M. Llinas, "Solution structure of the ε-aminohexanoic acid complex of human plasminogen kringle 1," *Eur. J. Biochem.*, 221(3): 939-949 (1994).

Schwartz, R.M., and M.O. Dayhoff, "Matrices for Detecting Distant Relationships," *Atlas of Protein Sequence and Structure*, 5(3): 353-358 (1978).

Shi, G-Y., et al., "Kringle Domains and Plasmin Denaturation," *Biochem. Biophys. Res. Comm.*, 178(1): 360-368 (1991).

Smith, L.J., et al., "Human Interleukin 4: The Solution Structure of a Four-helix Bundle Protein," *J. Mol. Biol.*, 224: 899-904 (1992).

Smith, T.F., and Michael S. Waterman, "Comparison of Biosequences," *Advances in Applied Mathematics*, 2: 482-489 (1981).

Sottrup-Jensen, L., et al., "The Primary Structure of Human Plasminogen: Isolation of Two Lysine-Binding Fragments and One "Mini-" Plasminogen (MW, 38,000) by Elastase-Catalyzed-Specific Limited Proteolysis," *Prog. Chem. Fibrinol. Thrombol.*, 3: 191-209 (1978).

Stewart, D., et al., "Distinct dose-dependent effects of plasmin and TPA on coagulation and hemorrhage," *Blood*, 101(8): 3002-3007 (2003).

Thewes, T., et al., "Ligand Interactions with the Kringle 5 Domain of Plasminogen," *J. Biol. Chem.*, 265(7): 3906-3915 (1990).

Van Zonneveld, A-J., et al., "Autonomous functions of structural domains on human tissue-type plasminogen activator," *PNAS*, 83: 4670-4674 (1986).

Wiman, B. and Désiré Collen, *Nature*, 272: 549-550 (1978).

Wiman, B. and Désiré Collen, "On the Kinetics of the Reaction between Human Antiplasmin and Plasmin," *Eur. J. Biochem.*, 84: 573-578 (1978).

Wiman, B., et al., "On the Specific Interaction Between the Lysine-Binding Sites in Plasmin and Complementary Sites in $α_2$—Antiplasmin and in Fibrinogen," *Biochim. Biophys. Acta*, 579: 142-154 (1979).

Wohl, R.C., et al., "Kinetics of Activation of Human Plasminogen by Different Activator Species at pH 7.4 and 37° C.," *J. Biol. Chem.*, 255(5): 2005-2013 (1980).

Wohl, R.C., et al., "Steady State Kinetics of Activation of Human and Bovine Plasminogens by Streptokinase and Its Equimolar Complexes with Various Activated Forms of Human Plasminogen," *J. Biol. Chem.*, 253(5): 1402-1407 (1978).

Wu, T.P., et al., "The structure of recombinant plasminogen kringle 1 and the fibrin binding site," *Blood Coagul. Fibrinolysis*, 5(2): 157-166 (1994).

Zajicek, J., et al., "The Effects of Ligand Binding on the Backbone Dynamics of the Kringle 1 Domain of Human Plasminogen," *J. Mol. Biol.*, 301(2): 333-347 (2000).

Medynski, D., et al., "Refolding, purification, and activation of miniplasminogen and microplasminogen isolated from *E. coli* inclusion bodies," *Protein Expression and Purification* 52: 395-402 (2007).

Wang, S., et al., "Deletion of Ile 1 Changes the Mechanism of Streptokinase: Evidence for the Molecular Sexuality Hypothesis," *Biochemistry*, 38: 5232-5240 (1999).

Bhisitkul, R.B., "Anticipation for Enzymatic Vitreolysis," *Br. J. Ophthalmol.*, 85: 1-3 (2001).

Gandorfer, A., et al., "Ultrastructure of the viteoretinal interface following plasmin assisted vitrectomy," *Br. J. Ophthalmol.*, 85: 6-10 (2001).

Gandorfer, A., et al., "Posterior Vitreous Detachment Induced by Microplasmin," *OVS*, 45(2): 641-641 (2004).

Horrevoets, A.J.G., et al., "Production and Characterization of Recominant Human Plasminogen (S741C-Fluorescein): A Novel Approach to Study Zymogen Activation Without Generation of Active Protease," *J. Bio. Chem.*, 272(4): 2176-2182 (1997).

Horrevoets, A.J.G., et al., "The Activation-resistant Comformation of Recombinant Human Plasminogen Is Stabilized by Basic Residues in the Amino-terminal Hinge Region," *J. Bio. Chem.*, 270(26): 15770-15776 (1995).

Li, X., et al., "Posterior Vitreous Detachment with Plasmin in the isolated Human Eye," *Graefe's Arch. Clin. Exp. Ophthalmol.*, 240:56-62 (2002).

Trese, M.T., "Enzymatic Vitreous Surgery," *Seminars in Ophthalmology*, 15(2): 116-121 (2000).

Verstraeten, T.C., et al., "Pharmacologic Induction of Posterior Vitreous Detachment in the Rabbit," *Arch Ophthalmol.*, 111: 849-854 1993.

Wang, F., et al., "Safety and Efficacy of Displase and Plasmin in Pharmacologic Vitreolysis," *OVS*, 45(9): 3286-3290 (2004).

Wang, Z-L, et al., "PVD Following Plasmin But Not Hyaluronidase: Implications for Combination Pharmacologic Vitreolysis Therapy," *Retina*, 25: 38-43 (2005).

Williams, J.G., et al., "Autologous Plasmin Enzyme in the Surgical Management of Diabetic Retinopathy," *Ophthalmology* 108(10): 1902-1905 (2001).

Hunt, J.A., et al., "Simplified Recombinant Plasmin: Production and Functional Comparison of a Novel Thrombolytic Molecule with Plasma-Derived Plasmin," *Thromb. Haemost.*, 100: 413-419 (2008).

Marder, V.J., et al., "Haemostatic Safety of a Unique Recombinant Plasmin Molecule Lacking Kringles 2-5," *Thromb. Haemost.*, 104: 780-787 (2010).

Patthy, L., et al., "Evolution of the Proteases of Blood Coagulation and Fibrinolysis by Assembly from Modules," *Cell* 41:657-663 (1985).

Madison, E.L., "Probing Structure-Function Relationships of Tissue-Type Plasminogen Activator by Site-Specific Mutagenesis," *Fibrinolysis* 8 Supp.1:221-236 (1994).

Wang, J., et al., "Structure and Function of Microplasminogen: I. Methionine Shuffling, Chemical Proteolysis, and Proenzyme Activation," *Protein Sci.* 4:1758-1767 (1995).

Christensen, S., et al., "Stopped-Flow Fluorescence Kinetics of Bovine α2-Antiplasmin Inhibition of Bovine Midiplasmin," *Biochem. J.* 305:97-102 (1995).

Obukowicz, M.G., et al., "Secretion of Active Kringle-2—Serine Protease in *Escherichia coli*," *Biochemistry* 29:9737-9745 (1990).

Söohndel, S., et al., "Recombinant Gene Expression and 1H NMR characteristics of the Kringle (2+3) Supermodule: Spectroscopic/Functional Individuality of Plasminogen Kringle Domains," *Biochemistry* 35:2357-2364 (1996).

Wu, S-C., et al., A Fast-Acting Modular-Structured Staphylokinase Fusion with Kringle-1 From Human Plasminogen as the Fibrin-Targeting Domain Offers Improved Clot Lysis Efficacy, *J. Biol. Chem.* 278(20):18199-181206 (2003).

Novokhatny, V., et al., "Domain Structure and Domain-Domain Interaction of recombinant Tissue Plasminogen Activator," *J. Biol. Chem.* 266(20):12994-13002 (1991).

Langer-Safer, P.R., et al., "Replacement of Finger and Growth Factor Domains of Tissue Plasminogen Activator with Plasminogen Kringle 1," *J. Biol. Chem.* 265(6):3715-3723 (1991).

Burgin, J. and J. Sheller, "Expression, Isolation and Characterization of a Mutated Human Plasminogen Kringle 3 with a Functional Lysine Binding Site," *Cell. Mol. Life. Sci.* 55: 135-141 (1999).

Deutsch, D.G and E. T. Mertz, "Plasminogen Purification from Human Plasma by Affinity Chromatography," *Science* 107:1095-1096 (1970).

Mukhopadhyay, A., "Inclusion Bodies and Purification of Proteins in Biologically Active Forms," *Advances in Bio. Eng./Biotech.* 56:61-109 (1997).

\* cited by examiner

FIG. 3

```
-19                    1
MEHKEVVLLLLLFLKSGQGEPLDDYVNTQGASLFSVTKKQLGAGSIEECAAKCEEDEEFTCRAFQ

78
YHSKEQQCVIMAENRKSSIIIRMRDVVLFEKKVYLSECKTGNGKNYRGTMSKTKNGITCQKWSST 136      143       153       162
SPHRPRFSPATHPSEGLEENYCRNPDNDPQGPWCYTTDPEKRYDYCDILECEEECMHCSGENYDG
       kringle 1

KISKTMSGLECQAWDSQSPHAHGYIPSKFPNKNLKKNYCRNPDRELRPWCFTTDPNKRWELCDIP
              kringle 2

RCTTPPPSSGPTYQCLKGTGENYRGNVAVTVSGHTCQHWSAQTPHTHNRTPENFPCKNLDENYCR
                                        kringle 3

NPDGKRAPWCHTTNSQVRWEYCKIPSCDSSPVSTEQLAPTAPPELTPVVQDCYHGDGQSYRGTSS

TTTTGKKCQSWSSMTPHRHQKTPENYPNAGLTMNYCRNPDADKGPWCFTTDPSVRWEYCNLKKCS
             kringle 4

GTEASVVAPPPVVLLPDVETPSEEDCMFGNGKGYRGKRATTVTGTPCQDWAAQEPHRHSIFTPET
                                                       kringle 5

542
NPRAGLEKNYCRNPDGDVGGPWCYTTNPRKLYDYCDVPQCAAPSFDCGKPQVEPKKCPGRVVGGC

VAHPHSWPWQVSLRTREGMHFCGGTLISPEWVLTAAHCLEKSPRPSSYKVILGAHQEVNLEPHVQ

EIEVSRLFLEPTRKDIALLKLSSPAVITDKVIPACLPSPNYVVADRTECFITGWGETQGTFGAGL

LKEAQLPVIENKVCNRYEFLNGRVQSTELCAGHLAGGTDSCQGDSGGPLVCFEKDKYILQGVTSW
           791
GLGCARPNKPGVYVRVSRFVTWIEGVMRNN       (SEQ ID NO:4)
```

FIG. 4

```
HK1  CKTGNGKNYR  GTMSKTKNGI  TCQKWSSTSP  HR-PRFSPAT  HPSEGLEENY
HK2  CMHCSGENYD  GKISKTMSGL  ECQAWDSQSP  HA-HGYIPSK  FPNKNLKKNY
HK3  CLKGTGENYR  GNVAVTVSGH  TCQHWSAQTP  HT-HNRTPEN  FPCKNLDENY
HK4  CYHGDGQSYR  GTSSTTTTGK  KCQSWSSMTP  HR-HQKTPEN  YPNAGLTMNY
HK5  CMFGNGKGYR  GKRATTVTGT  PCQDWAAQEP  HRHSIFTPET  NPRAGLEKNY (con't)
HK1  CRNPDNDPQG  PWCYTTDPEK  RYDYCDILEC  (SEQ ID NO:5)
HK2  CRNPDRE-LR  PWCFTTDPNK  RWELCDIPRC  (SEQ ID NO:6)
HK3  CRNPDGK-RA  PWCHTTNSQV  RWEYCKIPSC  (SEQ ID NO:7)
HK4  CRNPDAD-KG  PWCFTTDPSV  RWEYCNLKKC  (SEQ ID NO:8)
HK5  CRNPDGVGG   PWCYTTNPRK  LYDYCDVPQC  (SEQ ID NO:9)
```

FIG. 5

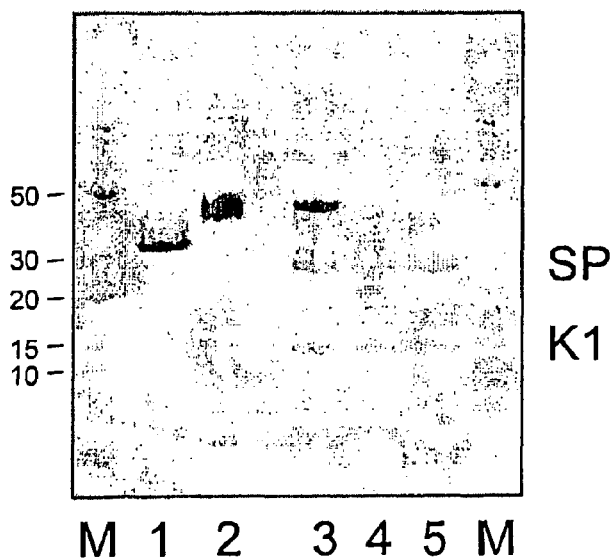

Plasmin:
Km 193 +/- 7 μM
$k_{cat}$: 760 min$^{-1}$

Mini-plasmin:
Km 160 +/- 30 μM
$k_{cat}$: 770 min$^{-1}$

Micro-plasmin:
Km 145 +/- 13 μM
$k_{cat}$: 795 min$^{-1}$

Delta-plasmin:
Km 138 +/- 5 μM
$k_{cat}$: 755 min$^{-1}$

RECOMBINANTLY MODIFIED PLASMIN

RELATED APPLICATIONS

The present application is a National Phase Application under §371 of International Application Serial Number PCT/US05/13562 filed on Apr. 21, 2005, which claims benefit of priority to Provisional Application Ser. No. 60/564,472, filed on Apr. 22, 2004 the contents of which are herein incorporated by reference in its entirety.

BACKGROUND OF THE INVENTION

Human plasminogen is a single-chain protein containing 791 amino acid residues. Activation of plasminogen to plasmin results from a single cleavage of the Arg561-Val562 peptide bond in the zymogen. The resulting plasmin molecule is a two-chain, disulfide-linked serine protease with trypsin-like specificity (cleaves after Lys and Arg).

The amino-terminal heavy chain of plasmin (residues 1-561, ~60 kDa) is composed of five kringle domains, each containing approximately 80 amino acid residues. The kringle domains are responsible for the regulatory properties of plasminogen, such as interaction with activation inhibitors, e.g., $Cl^{-1}$ ions; with activation stimulators, e.g., $\epsilon$-aminocaproic acid; with mammalian and bacterial cells; and with other proteins, such as plasmin physiological substrate fibrin and plasmin inhibitor α2-antiplasmin. Of all five kringles, kringle 1 is one of the most multi-functional: its lysine-binding activity has been shown to be responsible for plasmin interaction with α2-antiplasmin and fibrin. See Wiman, B., et al., *Biochim. Biophys. Acta* 579:142-154 (1979); and Lucas, M. A., et al., *J. Biol. Chem.* 258:4249-4256 (1983).

The C-terminal light chain of plasmin (residues 562-791, ~25 kDa) is a typical serine protease, homologous to trypsin and containing the classic serine protease catalytic triad: His603, Asp646 and Ser741. Plasminogen contains 24 disulfide bridges and 2 glycosylation sites, on Asn289 and Thr346.

The limited proteolysis of plasminogen by elastase has been shown to result in three fragments (Sottrup-Jensen, L., et al., *Prog. Chem. Fibrinol. Thrombol.*, 3:191-209 (1978)). First fragment, K1-3, includes the first three kringles and can be isolated in two versions, Tyr79-Val338 and Tyr79-Val354. The second fragment, K4, corresponds to the fourth kringle and includes residues Val355-Ala440. The last, C-terminal fragment (the so-called mini-plasminogen) includes residues Val443-Asn791 and consists of the fifth kringle and the serine protease domain. Mini-plasminogen can be activated in the same way as plasminogen, forming mini-plasmin.

Because of the complex structure of the full-length plasminogen molecule, bacterial expression systems have not proven useful for recombinant plasminogen production. Plasminogen is produced in the form of insoluble inclusion bodies and is not re-foldable from that state. Further, the expression of plasminogen in mammalian cells is complicated by intracellular activation of plasminogen into plasmin and the resulting cytotoxicity. Production of fully active plasminogen using insect cells is possible, however, this system is not suitable for large-scale production due to low yield.

Accordingly, a modified recombinant protein, possessing the desirable characteristics of plasmin/plasminogen while lacking certain negative characteristics and to being capable of production in bacterial cells in substantial quantities, is desirable.

SUMMARY OF THE INVENTION

The present invention provides a polynucleotide comprising a nucleotide sequence encoding a polypeptide having a single N-terminal kringle domain homologous to a kringle domain of native human plasminogen; and a C-terminal domain activation site and serine protease domain homologous to the corresponding domains in human plasminogen; wherein the polypeptide binds to immobilized lysine. The N-terminal kringle domain can be homologous to kringle 1 or kringle 4 of native human plasminogen.

In some embodiments, the encoded polypeptide is at least 90%, 95%, or 98% identical to the sequence shown in SEQ ID NO:2. Further, the encoded polypeptide can be the sequence shown in SEQ ID NO:2.

The nucleotide sequence of the polynucleotide can be the sequence shown in SEQ ID NO:1 or degenerate variations thereof. The nucleotide sequence can encode a polypeptide having an N-terminal kringle domain homologous to the kringle 1 or kringle 4 domain of native human plasminogen; and a C-terminal domain activation site and serine protease domain homologous to the corresponding domains in human plasminogen. The nucleotide sequence can also encode a polypeptide having a single N-terminal kringle domain at least 90% identical to the kringle 1 or kringle 4 domain of native human plasminogen; and a C-terminal domain at least 90% identical to the activation site and serine protease domain of human plasminogen. The encoded polypeptides can bind immobilized lysine.

In another aspect, the invention provides polypeptides having an N-terminal kringle domain homologous to a kringle domain of native human plasminogen; and a C-terminal domain activation site and serine protease domain homologous to the corresponding domains in human plasminogen.

In some embodiments, the polypeptides can have an N-terminal kringle domain homologous to kringle 1 or kringle 4 of native human plasminogen.

In some embodiments, the polypeptides can exhibit a fibrinolytic activity that is inhibited by $\alpha_2$-antiplasmin at a rate that is at least about 5-fold faster than the rate of inhibition of the fibrinolytic activity of mini-plasmin by $\alpha_2$-antiplasmin. The rate of inhibition by $\alpha_2$-antiplasmin can also be at least about 10-fold, 20-fold, 30-fold, or 40-fold faster than the rate of inhibition of mini-plasmin.

In some embodiments, the polypeptides can bind immobilized lysine. The immobilized lysine can be lysine bound to a solid support matrix selected from the group consisting of lysine-agarose, lysine-BIOGEL (BioRad, Hercules, Calif.), lysine-HYPERD (Pall Life Sciences, East Hills, N.Y., a lysine-hydrogel), lysine-SEPHAROSE (SEPHAROSE is cross-linked agarose). The immobilized lysine can be lysine-SEPHAROSE.

In some embodiments, the polypeptides can exhibit a lower binding affinity for fibrinogen than the binding affinity for fibrinogen of mini-plasmin.

In some embodiments, the polypeptides can exhibit higher binding affinity for partially cleaved fibrin than the binding affinity for partially cleaved fibrin of mini-plasmin.

In some embodiments, the polypeptides can have a single kringle domain located N-terminal to a plasminogen activation site and plasminogen serine protease domain, wherein the kringle domain has at least one residue greater amino acid sequence identity with kringle 1 or kringle 4 of native human plasminogen than with kringle 5 of native human plasminogen. For these embodiments, it will be understood that conservative substitutions of the kringle regions of the polypeptides of the invention, relative to the native sequences of kringles 1 and 4 of human plasminogen, would not be considered as differing from the native sequences for purposes of the identity comparison with kringle 5.

In some embodiments, the polypeptides can have the amino acid sequence as shown in SEQ ID NO:2, and conservative substitutions thereof. The polypeptides can have a residue at a relative position analogous to that of position 76 of the amino acid sequence shown in SEQ ID NO: 2 that is arginine.

In another aspect, the invention includes vectors comprising the polynucleotides of the invention, and cultured host cells comprising the vectors.

BRIEF DESCRIPTION OF THE DRAWINGS

FIG. 3 shows the amino acid sequence of human plasminogen, showing the 19-residue leader sequence numbered as −19 to −1, and the plasminogen sequence shown as residues 1-791 (see SEQ ID NO:3 (cDNA sequence for human plasminogen; and SEQ ID NO:4, the encoded amino acid sequence, as shown in FIG. 3). A number of features are shown, including the following: the delta-plasminogen sequence (shaded); kringle domains 1-5 (double underscore); glycosylations sites Asn289 and Thr346 (in bold); the plasminogen activation Arg-Val activation site (in bold); and lysine-binding sites in kringle 1 (in underscore and with specific position numbering).

FIG. 4 shows polypeptide sequence comparisons between the five kringle domains (1-5) of native human plasmin(ogen). Amino acid residues that are identical to those of the same relative position in kringle 1 are shown in underscore.

FIG. 5 shows a 8-25% gradient SDS-PAGE of a non-reduced (Lane 1) and reduced (Lane 2) delta-plasminogen preparation. Activation of delta-plasminogen into delta-plasmin with streptokinase (Lane 3), tissue Plasminogen Activator (tPA) (Lane 4), and urokinase (Lane 5) results in the formation of the two-chain molecule consisting of kringle 1 (K1) and the serine protease domain (SP) connected by two disulfide bridges.

DESCRIPTION OF THE INVENTION

Figure 1:
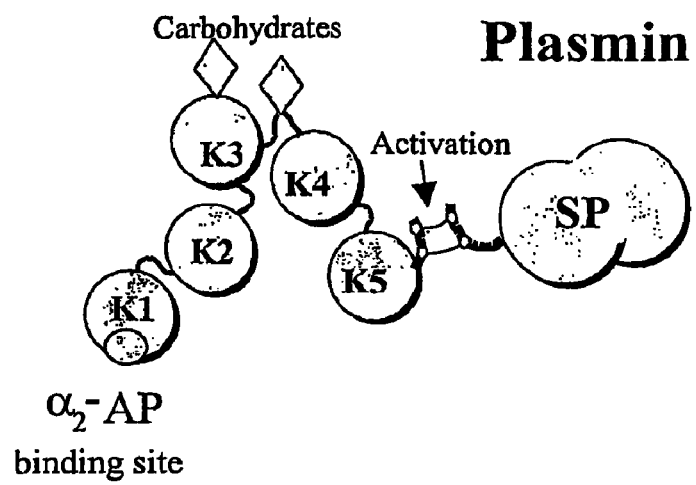
FIG. 1 is a schematic representation of native plasmin after activation by proteolytic cleavage. K1-K5 are kringle regions 1-5; and SP is the serine protease domain. "α2-AP" is the α$_2$-antiplasmin binding site on kringle 1.
Figure 2:
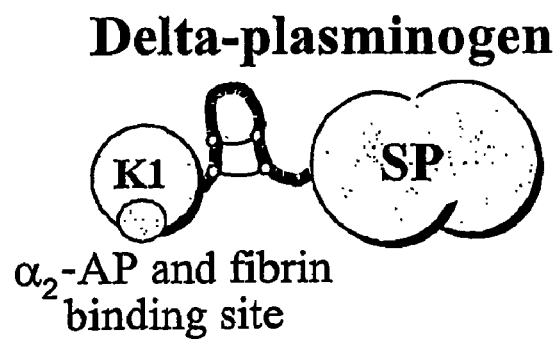
FIG. 2 is a schematic representation of a plasminogen deletion mutant of the invention using the same nomenclature as in FIG. 1, and showing the deletion of K2-5.

In order to provide a simple, non-glycosylated molecule having the fibrin- and antiplasmin-binding properties of full-length plasmin, the present invention provides a deletion mutant of plasminogen. In this mutant, referred to herein as delta-plasminogen, at least a portion of the native amino acid sequence between a domain homologous to kringle 1 and the activation site is deleted. In one aspect, the domain homologous to the native kringle 1 domain of human plasminogen can be directly attached to the serine protease portion of plasminogen, or an homologous, functional analog thereof, with substantially only the intervening native sequence containing the plasminogen activation site remaining between the domains.

Delta-plasmin(ogen) according to the present invention can be characterized by: lower molecular weight (37,198 Da) of delta-plasmin can result in increased to specific activity (per mg of protein); the lack of at least two glycosylation sites found in the native protein (see FIG. 3), combined with the relatively low molecular weight, can facilitate recombinant production of this protein using relatively inexpensive bacterial and yeast expression systems; delta-plasminogen can be activated by plasminogen activators tPA, urokinase, and streptokinase; the presence of the domain homologous to native kringle 1 preserves the fibrin-binding properties of plasmin which can be important for thrombolytic efficacy; presence of α2-antiplasmin-binding sites on the domain homologous to kringle 1 can allow delta-plasmin to be inhibited rapidly by this physiological inhibitor of plasmin (a feature which can prevent bleeding); the smaller size of delta-plasmin can facilitate its inhibition by α$_2$-macroglobulin, further lessening the chance of bleeding complications relative to native plasmin. In particular embodiments, the absence of kringle 5, which retains the primary binding site for intact, undigested fibrin(ogen), can allow use of delta-plasmin with reduced depletion of circulating fibrinogen.

Generally, the invention provides recombinant plasmin(ogen) molecules having a single kringle region N-terminal to the activation site and serine protease domain, having certain advantages relative to mini-plasmin(ogen). Although the delta-plasminogen polypeptides of the invention only have one kringle region, as such, N-terminal to the activation site, some embodiments include additional sequences N-terminal to the activation site. Additional N-terminal sequences can be derived from those of native kringle regions of plasminogen.

The N-terminal kringle domains of the present invention include kringle sequences of kringles 1 and 4 of native plasmin(ogen) and functional equivalents thereof. In particular, see the discussion below which provides guidance regarding preservation of function in polypeptide variants, including preservation of residues participating in or influencing lysine-binding.

DEFINITIONS

The terms "domain" and "region" of a polypeptide are generally synonymous as used herein, unless otherwise indicated to the contrary. When recited together with well-recognized structural or functional designations such as "kringle" or "serine protease," etc., such terms will introduce a polypeptide feature relating to at least some characteristic(s) commonly recognized and understood to be associated with the polypeptide structures corresponding to such designations.

A "cultured host cell," as used herein, refers to a prokaryotic or eukaryotic cell that contains heterologous DNA that has been introduced into the cell by any means, e.g., electroporation, calcium phosphate precipitation, microinjection, transformation, viral infection, and the like.

"Heterologous" as used herein means "of different natural origin" or representing a non-natural state. For example, if a cultured host cell is transformed with a DNA or gene derived from another organism, particularly from another species, that gene is heterologous with respect to that cultured host cell and also with respect to descendants of the cultured host cell which carry that gene. Similarly, "heterologous" refers to a nucleotide sequence derived from and inserted into the same natural, original cell type, but which is present in a non-natural state, e.g., a different copy number or under the control of different regulatory elements.

A "vector" molecule is a nucleic acid molecule into which heterologous nucleic acid can be inserted which can then be introduced into an appropriate cultured host cell. Vectors preferably have one or more origins of replication, and one or more sites into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes."

As used herein, the term "transcriptional control sequence" refers to nucleic acid sequences, such as initiator sequences, enhancer sequences and promoter sequences, which induce, repress, or otherwise control the transcription of protein encoding nucleic acid sequences to which they are operably-linked.

The term "polypeptide" is used interchangeably herein with the terms "peptide" and "protein."

The terms "polynucleotide" and "nucleic acid" are used interchangeably herein, and can refer to any nucleic acid that contains the information necessary for the purpose indicated by the context. That is, the nucleic acid can be DNA or RNA, either single stranded or double stranded, or other nucleic acid, as long as the polymer is capable of representing the appropriate information, e.g., in relation to an encoded peptide, and can include complementary sequences, e.g., sense strands and anti-sense strands of nucleic acids polymers.

The term "variant" of a polypeptide refers to an amino acid sequence that is altered by one or more amino acids. The variant can have "conservative" changes, wherein a substituted amino acid has similar structural or chemical properties, e.g., replacement of leucine with isoleucine. Alternatively, a variant can have "non-conservative" changes, e.g., replacement of a glycine with a tryptophan. Analogous minor variation can also include amino acid deletion or insertion, or both. A particular form of a "variant" polypeptide is a "functionally equivalent" polypeptide, i.e., a polypeptide which exhibits substantially similar in vivo or in vitro activity as the examples of the polypeptide of invention, as described in more detail below. Guidance in determining which amino acid residues can be substituted, inserted, or deleted without eliminating biological or immunological activity can be found using computer programs well-known in the art, for example, DNASTAR software (DNASTAR, Inc., Madison, Wis.). Further, specific guidance is provided below, including that provided within the cited references which are fully incorporated herein by reference.

The terms "N-terminal" and "C-terminal" are used herein to designate the relative position of any amino acid sequence or polypeptide domain or structure to which they are applied. The relative positioning will be apparent from the context. That is, an "N-terminal" feature will be located at least closer to the N-terminus of the polypeptide molecule than another feature discussed in the same context (the other feature possible referred to as "C-terminal" to the first feature). Similarly, the terms "5'-" and "3'-" can be used herein to designate relative positions of features of polynucleotides.

The delta-plasminogen/plasmin polypeptides referred to herein as having a N-terminal domain "homologous to a kringle domain of native human plasminogen" exhibit structural and functional characteristics similar to native kringle domains of plasminogen. Further, the delta-plasminogen/plasmin polypeptides referred to herein as having a N-terminal domain "homologous to kringle 1" exhibit characteristics similar to native kringle 1, at least to the extent that the polypeptides can have a higher affinity for ω-aminocarboxylic acids (and functional homologs such as trans-4-aminomethylcyclohexane-1-carboxylic acid, a cyclic acid) than kringle 5. See, e.g., Chang, Y., et al., *Biochemistry* 37:3258-3271 (1998), incorporated herein by reference, for conditions and protocols for comparison of binding of isolated kringle domain polypeptides to 5-aminopentanoic acid (5-APnA); 6-aminohexanoic acid (6-AHxA), also known as ε-aminocaprioic acid (εACA); 7-aminoheptanoic acid (7-AHpA); and trans-4-aminomethylcyclohexane-1-carboxylic acid (t-AMCHA).

References to kringle domains "homologous to kringle 4" are defined similarly, as noted above regarding the phrase "homologous to kringle 1." That is, they exhibit functional characteristics similar to kringle 1 of native human plasminogen as discussed above. These polypeptides also bind immobilized lysine as described above.

The polypeptides of the invention bind immobilized lysine. As used herein, the phrase "binding immobilized lysine" means that the polypeptides so characterized are retarded in their progress relative to mini-plasminogen when subjected to column chromatography using lysine-SEPHAROSE as the chromatographic media. Typically, the polypeptides of the invention can be eluted from such chromatographic media (lysine affinity resins) using solutions containing the specific ligand, e.g., εACA, as eluants.

Further, in addition to Chang et al., supra, other references can be consulted by those of skill in the art to determine which residues can be varied by conservative or non-conservative substitution, deletion or addition to yield a deletion mutant within the scope of the present invention. For example, the following references provide information regarding particular residues of the native kringle domains that may be important for binding of ω aminocarboxylic acids: U.S. Pat. No.

6,538,103 to Ji, et al.; U.S. Pat. No. 6,218,517 to Suzuki; Douglas, J. T., et al., *Biochemistry* 41(10):3302-10 (2002); Zajicek, J., et al., *J. Mol. Biol.,* 301(2):333-47 (2000); Lee, H., et al., *Arch Biochem Biophys.,* 375(2):359-63 (2000); Castellino, F. and S. McCance, *Ciba Found Symp.* 212:46-60 (1997); McCance, S., et al., J. Biol. Chem., 269:32405-32410 (1994); Rejante, M. R. and M. Llinas, *Eur. J. Biochem.,* 221 (3):939-49 (1994); Wu, T. P., et al., *Blood Coagul. Fibrinolysis,* 5(2):157-66 (1994); Hoover, C. J., et al., *Biochemistry,* 32(41):10936-43 (1993); Menhart, N., et al., *Biochemistry,* 32:8799-8806 (1993); Thewes, T., et al., *J. Biol. Chem.,* 265 (7):3906-3915 (1990); Novokhatny, V., et al., *Thromb Res.,* 53(3):243-52 (1989); Motta, A., et al., *Biochemistry,* 26(13): 3827-36 (1987); Novokhatny, V., et al., *J. Mol. Biol.,* 179:215-232 (1984); Lerch, P. G., et al., *Eur. J. Biochem.,* 107(1):7-13 (1980); Sottrup-Jensen, L., et al., *Prog. Chem. Fibrinol. Thrombol,* 3:191-209 (1978); and Wiman, B. and D. Collen, *Nature* 272, 549-545 (1978), all incorporated herein by reference in their entirety.

Because the present inventors have recognized that a valuable, simplified plasmin(ogen) molecule can be prepared having an N-terminal kringle domain having advantageous functional characteristics (which can be evaluated, in part, by testing for the binding of immobilized lysine as described herein), the present invention can encompass other fibrin-binding domains or regions N-terminal to the activation site. For example, the invention can include polypeptides in which the serine protease domain of plasmin is attached to a fibrin-binding kringle selected from a group including, but not limited to, kringle 4 of human plasminogen, kringle 2 of tPA, or a kringle of apolipoprotein (a). Further, the invention can include polypeptides in which a serine protease domain of plasmin is attached to any other known fibrin-binding modules, such as the "finger" domain of tPA or fibronectin, or the FAB fragment of fibrin-specific IgG.

In particular embodiments, residues at certain positions of the N-terminal kringle domain of delta-plasminogen are conserved relative to kringle 1 of native human plasminogen. These can be residues at positions associated with lysine binding, and include Pro136-Pro140, Pro143-Tyr146, and Arg153-Tyr156 (positions numbered as shown in FIG. 3). Some embodiments of the delta-plasminogen of the invention can have Arg at position 153. In other embodiments, the specific positions of the named residues can vary somewhat while still being present in the polypeptide at structurally and functionally analogous positions (i.e. relative to the kringle structure of the N-terminal domain; see Chang, Y., et al. as discussed above). In some embodiments, the N-terminal kringle region of the delta-plasmin(ogen) polypeptide has at least one residue greater percent identity with kringle 1 or kringle 4 of native human plasminogen than with kringle 5 of native human plasminogen.

Additionally, particular embodiments of the invention can be characterized functionally by contrast to mini-plasmin (ogen) which has a similar domain composition, i.e., kringle-serine protease (K-SP) (see Sottrup-Jensen, L., et al., Progress in Chemical Fibrinolysis and Thrombolysis, Vol. 3, (Eds: J. F. Davidson, et al.) Raven Press, New York (1978)). In preferred embodiments, the delta-plasmin of the invention exhibits an increased rate of inhibition by $\alpha_2$-antiplasmin, e.g., as much to as about one or two orders of magnitude faster than the rate of inhibition of mini-plasmin. Further, in particular embodiments, delta-plasmin binds immobilized lysine (e.g., lysine-SEPHAROSE).

Characterization of the kringle domain of delta-plasminogen as "N-terminal" means only that the domain is present N-terminal to the activation site and does not mean that additional amino acids residues N-terminal to the domain itself are not present. Further, the number and identity of residues interposed between the domain homologous to kringle 1 and the activation site of plasminogen can be varied without departing from the scope of the present invention. One of skill in the art will be able to determine these variations that achieve the benefits of the invention (kringle 1-like binding of co aminocarboxylic acids, without substantial increase in size of the deletion mutant or introduction of potentially problematic glycosylation sites) without undue experimentation based on the disclosure herein and the references cited herein for guidance regarding kringle 1 function and structure.

Accordingly, the invention relates to polynucleotides, polypeptides, recombinant methods for producing the polypeptides, vectors containing the polynucleotides, expression systems for producing the polypeptides, and cultured host cells comprising such expression systems.

As noted, in one aspect, the invention relates to a polynucleotide encoding the polypeptide disclosed herein or a polypeptide having conservative amino acid substitutions thereof. Guidance regarding selection of "conservative" amino acid substitutions is provide in more detail below. In one embodiment, the polynucleotide is DNA.

In another aspect, the invention relates to a method of making a vector comprising inserting the polynucleotide of the invention into a vector. In another aspect, the invention relates to a vector produced by the method of the invention.

In another aspect, the invention relates to a method of making a cultured host cell comprising introducing the vector of the invention into a cultured host cell. In another aspect, the invention relates to a cultured host cell produced by the method of the invention.

In another aspect, the invention relates to an isolated polypeptide of the invention, produced by a method comprising: (a) introducing a vector comprising a polynucleotide encoding the polypeptide into a cultured host cell; (b) culturing the host cell; and (c) recovering the polypeptide. In another aspect, the invention relates to a method for producing a polypeptide comprising: (a) culturing the host cell of the invention under conditions that the vector is expressed; and (b) recovering the polypeptide.

In another aspect, the invention relates to cells containing at least one polynucleotide of the invention.

In one embodiment, the polynucleotide comprises the nucleotide sequence as shown in SEQ ID NO:1. In another embodiment, the polypeptide comprises the amino acid sequence as shown in SEQ ID NO:2.

Polynucleotides

The polynucleotides of the invention include variants which have substitutions, deletions, and/or additions which can involve one or more nucleotides. The variants can be altered in coding regions, non-coding regions, or both. Alterations in the coding regions can produce conservative or non-conservative amino acid substitutions, deletions or additions. Especially preferred among these are silent substitutions, additions and deletions, which do not alter the properties and activities of the delta-plasmin(ogen) protein or portions thereof. Also especially preferred in this regard are conservative substitutions (see below).

Further embodiments of the invention include nucleic acid molecules comprising a polynucleotide having a nucleotide sequence at least 90% identical, and more preferably at least 95%, 96%, 97%, 98% or 99% identical to (a) a nucleotide sequence encoding the delta-plasminogen polypeptide having the complete amino acid sequence in SEQ ID NO: 2; (b) a nucleotide sequence encoding the delta-plasminogen polypeptide having the amino acid sequence in SEQ ID NO:2; and (c) a nucleotide sequence complementary to any of the nucleotide sequences in (a) or (b) above.

By a polynucleotide having a nucleotide sequence at least, for example, 95% "identical" to a reference nucleotide sequence encoding a delta-plasminogen polypeptide is intended that the nucleotide sequence of the polynucleotide be identical to the reference sequence except that the polynucleotide sequence can include up to five point mutations per each 100 nucleotides of the reference nucleotide sequence encoding the delta-plasminogen polypeptide. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

As noted above, two or more polynucleotide sequences can be compared by determining their percent identity. Two or more amino acid sequences likewise can be compared by determining their percent identity. The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An implementation of this algorithm for nucleic acid and peptide sequences is provided by the Genetics Computer Group (Madison, Wis.) in their BESTFIT utility application. The default parameters for this method are described in the Wisconsin Sequence Analysis Package Program Manual, Version 8 (1995) (available from Genetics Computer Group, Madison, Wis.).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the nucleic acid sequence shown in SEQ ID NO: 1 will encode a delta-plasminogen polypeptide. In fact, because degenerate variants of these nucleotide sequences all encode the same polypeptide, this will be clear to the skilled artisan even without performing any functional assays or measurements described herein It will be further recognized in the art that, for such nucleic acid molecules that are not degenerate variants, a reasonable number will also encode a polypeptide having delta-plasminogen polypeptide activity. This is because the skilled artisan is fully aware of amino acid substitutions that are either less likely or not likely to significantly effect protein function (e.g., replacing one aliphatic amino acid with a second aliphatic amino acid).

Recently, advances in the synthetic production of longer polynucleotide sequences have enabled the synthetic production of nucleic acids encoding significantly longer polypeptides without the use of traditional cloning techniques. Commercial providers of such services include Blue Heron, Inc., Bothell, Wash. (http://www.blueheronbio.com). Technology utilized by Blue Heron, Inc. is described in U.S. Pat. Nos. 6,664,112; 6,623,928; 6,613,508; 6,444,422; 6,312,893; 4,652,639; U.S. Published Patent Application Nos. 20020119456A1; 20020077471A1; and Published International Patent Applications (Publications Nos) WO03054232A3; WO0194366A1; WO9727331A2; and WO9905322A1, all incorporated herein by reference.

Of course, traditional techniques of molecular biology, microbiology, and recombinant nucleic acid can also be used to produce the polynucleotides of the invention. These techniques are well known and are explained in, for example, Current Protocols in Molecular Biology, F. M. Ausebel, ed., Vols. I, II and III (1997); Sambrook et al., Molecular Cloning: A Laboratory Manual, $2^{nd}$ Edition, Cold Spring Harbor Laboratory Press, Cold Spring Harbor, N.Y. (1989); DNA Cloning: A Practical Approach, D. N. Glover, ed., Vols. I and II (1985); Oligonucleotide Synthesis, M. L. Gait, ed. (1984); Nucleic Acid Hybridization, Hames and Higgins, eds. (1985); Transcription and Translation, Hames and Higgins, eds. (1984); Animal Cell Culture, R. I. Freshney, ed. (1986); Immobilized Cells and Enzymes, IRL Press (1986); Perbal, "A Practical Guide to Molecular Cloning"; the series, Methods in Enzymology, Academic Press, Inc. (1984); Gene Transfer Vectors for Mammalian Cells, J. H. Miller and M. P. Calos, eds., Cold Spring Harbor Laboratory (1987); and Methods in Enzymology, Wu and Grossman and Wu, eds., respectively, Vols. 154 and 155, all incorporated herein by reference.

Vectors and Cultured Host Cells

The present invention also relates to vectors which include the isolated nucleic to acid molecules of the present invention, cultured host cells which are genetically engineered with the recombinant vectors, and the production of the delta-plasmin (ogen) polypeptides by recombinant techniques.

Recombinant constructs can be introduced into cultured host cells using well-known techniques such as infection, transduction, transfection, transvection, electroporation and transformation. The vector can be, for example, a phage, plasmid, viral or retroviral vector. Retroviral vectors can be replication competent or replication defective. In the latter case, viral propagation generally will occur only in complementing cultured host cells.

The polynucleotides can be joined to a vector containing a selectable marker for propagation in a cultured host. Generally, a plasmid vector is introduced in a precipitate, such as a calcium phosphate precipitate, or in a complex with a charged lipid. If the vector is a virus, it can be packaged in vitro using an appropriate packaging cell line and then transduced into cultured host cells.

Preferred are vectors comprising cis-acting control regions to the polynucleotide of interest. Appropriate trans-acting factors can be supplied by the cultured host, supplied by a complementing vector or supplied by the vector itself upon introduction into the cultured host.

In certain embodiments in this regard, the vectors provide for specific expression, which can be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

DNA inserts should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate cultured hosts include, but are not limited to, bacterial cells, such as *E. coli, Streptomyces* and *Salmonella typhimurium* cells; fungal, cells, such as yeast cells; insect cells such as *Drosophila* S2 and *Spodoptera* Sf9 cells; animal cells such as CHO, COS and Bowes melanoma cells; and plant cells. Appropriate culture mediums and conditions for the above-described cultured host cells are known in the art.

Among vectors preferred for use in bacteria include pQE70, pQE60 and pQE-9, available from Qiagen Inc., Valencia, Calif.; pBS vectors, PHAGESCRIPT vectors, BLUESCRIPT vectors, pNH8A, pNH16a, pNH18A, pNH46A, available from Stratagene, LaJolla, Calif.; and ptrc99a, pKK223-3, pKK233-3, pDR540, pRIT5 available from Pharmacia (now Pfizer, Inc., New York, N.Y.). Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Bacterial promoters suitable for use in the present invention include the *E. coli* lacI and lacZ promoters, the T3 and T7 promoters; the gpt promoter, the lambda PR and PL promoters, and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of a vector construct into the cultured host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology, $2^{nd}$ Edition (1995).

Transcription of the DNA encoding the polypeptides of the present invention by higher eukaryotes can be increased by inserting an enhancer sequence into the vector. Enhancers are cis-acting elements of DNA, usually about from 10 to 300 bp that act to increase transcriptional activity of a promoter in a given cultured host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals can be incorporated into the expressed polypeptide. The signals can be endogenous to the polypeptide or they can be heterologous signals.

The polypeptide can be expressed in a modified form, such as a fusion protein, and can include not only secretion signals, but also additional heterologous functional regions. For instance, a region of additional amino acids, particularly charged amino acids, can be added to the N-terminus of the polypeptide to improve stability and persistence in the cultured host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP 0 464 533 A1 (Canadian counterpart, 2,045,869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties. On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery for example, human proteins have been fused with Fc portions for the to purpose of high-throughput screening assays (such as hIL5-receptor, to identify antagonists of hIL-5). See, Bennett, D., et al., *J. Molecular Recognition,* 8:52-58 (1995) and Johanson, K. et al., *J. Biol. Chem.,* 270(16):9459-9471. (1995).

Delta-plasminogen protein can be recovered and purified from recombinant cell cultures by well-known methods including those specifically described in the examples herein. Polypeptides of the present invention include naturally purified products, products of chemical synthetic procedures, and products produced by recombinant techniques from a prokaryotic or eukaryotic cultured host, including, for example, bacterial, yeast, higher plant, insect and mammalian cells. In addition, polypeptides of the invention can also include an initial modified methionine residue, in some cases as a result of host-mediated processes.

Polypeptides

The polynucleotides of the invention include those encoding variations and particular examples of the polypeptides of the invention. For example, guidance concerning how to make phenotypically silent amino acid substitutions is provided in Bowie, J. U. et al., "Deciphering the Message in Protein Sequences: Tolerance to Amino Acid Substitutions," *Science* 247:1306-1310 (1990), wherein the authors indicate that proteins are surprisingly tolerant of amino acid substitutions. Although any number of substitutions within the scope of the invention can be obtained by application of such general principles, for specific guidance regarding substitutions, the references cited herein regarding structure and function of kringle 1 domains can be consulted by one of skill in the art.

It will further be appreciated that, depending on the criteria used, the exact "position" of the kringle 1, activation site, and serine protease domains of the delta-plasminogen polypeptide can differ slightly in particular variations within the scope of the present invention. For example, the exact location of the kringle 1 domain relative to the activation site can vary slightly and/or the sequence N-terminal to the kringle 1 domain can vary in length. Thus, the invention includes such variations of the delta-plasminogen polypeptide which exhibit delta-plasminogen polypeptide activity as disclosed herein. Such variants include deletions, insertions, inversions, repeats, and substitutions. As indicated above, guidance concerning which amino acid changes are likely to be phenotypically silent can be found in Bowie, I. U., et al., "Deciphering the Message in Protein Sequences: Tolerance to Amino Acid Substitutions," Science 247:1306-1310 (1990).

Thus, fragments, derivatives or analogs of the polypeptide of SEQ ID NO: 2 can be (i) ones in which one or more of the amino acid residues (e.g., 3, 5, 8, 10, 15 or 20) are substituted with a conserved or non-conserved amino acid residue (preferably a conserved amino acid residue). Such substituted amino acid residues may or may not be one encoded by the genetic code, or (ii) ones in which one or more of the amino acid residues includes a substituent group (e.g., 3, 5, 8, 10, 15 or 20), or (iii) ones in which the mature polypeptide is fused with another compound, such as a compound to increase the half-life of the polypeptide (for example, polyethylene glycol), or (iv) ones in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

As indicated, changes are preferably of a minor nature, such as conservative amino acid substitutions that do not significantly affect the folding or activity of the protein. Of course, the number of amino acid substitutions a skilled artisan would make depends on many factors, including those described above. Generally speaking, the number of substitutions for any given delta-plasminogen polypeptide will not be more than 50, 40, 30, 25, 20, 15, 10, 5 or 3.

Amino acids in the delta-plasminogen polypeptide of the present invention that are essential for function can be identified by methods known in the art, such as site-directed mutagenesis or alanine-scanning mutagenesis (Cunningham and Wells, Science 244:1081-1085 (1989)). The latter procedure introduces single alanine mutations at every residue in the molecule. The resulting mutant molecules are then tested for biological activity, e.g., as shown in the examples provided herein. Sites that are critical for ligand binding can also be determined by structural analysis such as crystallization, nuclear magnetic resonance or photoaffinity labeling (Smith, et al., J. Mol. Biol. 224:399-904 (1992) and de Vos, et al. Science 255:306-312 (1992)). Even if deletion of one or more amino acids from the N-terminus of a protein results in modification or loss of one or more biological functions of the protein, other biological activities can still be retained.

It is also contemplated that polypeptides useful in production of the "isolated polypeptides" of the invention can produced by solid phase synthetic methods. See Houghten, R. A., Proc. Natl. Acad. Sci. USA 82:5131-5135 (1985); and U.S. Pat. No. 4,631,211 to Houghten et al. (1986).

The polypeptides of the present invention can be provided in an isolated form. By "isolated polypeptide" is intended a polypeptide removed from its native environment. Thus, a polypeptide produced and/or contained within a recombinant cultured host cell is considered isolated for purposes of the present invention. Also intended as an "isolated polypeptide" are polypeptides that have been purified, partially or substantially, from a recombinant cultured host.

Polypeptides having an amino acid sequence of an indicated percent identity to a reference amino acid sequence of a delta-plasminogen polypeptide can be determined using the methods, including computer-assisted methods, indicated above regarding polynucleotides. Polypeptide amino acid sequences are examined and compared just as are the nucleotide sequences in the foregoing discussion. One of skill in the art will recognize that such concepts as the molecular endpoints discussed for polynucleotides will have direct analogs when considering the corresponding use of such methods and programs for polypeptide analysis. For example, the manual corrections discussed regarding polynucleotides refer to 5' and 3' endpoints of nucleic acids, but the same discussion will be recognized as applicable to N-termini and C-termini of polypeptides.

The invention encompasses delta-plasminogen polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques, including but not limited, to specific chemical cleavage by cyanogen bromide, trypsin, chymotrypsin, papain, S. aureus V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition of an N-terminal methionine residue as a result of vectors and constructs adapted for expression of delta-plasminogen polypeptides in prokaryotic cultured host cells. The polypeptides can also be modified with a detectable label, such as an enzymatic, fluorescent, isotopic or affinity label to allow for detection and isolation of the protein.

Pharmaceutical Compositions and Methods of Treatment

Delta-plasmin(ogen) can be formulated for therapeutic use in accordance with the methods and compositions described in US 2003/0012778 A1; and Novokhatny, V., et al., J. Thromb. Haemost. 1(5):1034-41 (2003), both incorporated herein by reference. For example, a low-pH (from about 2.5 to about 4), low-buffering capacity buffer can be used for formulation of delta-plasmin. Additionally, other methods and formulations known to those of skill in the art, as practiced with plasmin, mini-plasmin, and/or micro-plasmin, can be used to formulate the delta-plasmin of the invention for therapeutic administration.

The delta-plasmin(ogen) can be used to treat a variety of thrombotic diseases or conditions, for example, according to the methods as described in U.S. Pat. No. 6,355,243; and published U.S. Patent Application Nos. US 2003/0026798 A1; US 2003/0175264 A1, all incorporated herein by reference. Again, as with the possible pharmaceutical formulations applicable to delta-plasmin, delta-plasmin can also be administered therapeutically by methods known in the art, for example, those that may be currently practiced with plasmin, mini-plasmin, and/or micro-plasmin.

EXAMPLES

Expression Vector Design

The amino acid sequence for delta-plasminogen is shown in SEQ ID NO:2. A putative sequence encoding delta-plasminogen was codon-optimized for E. coli expression and mRNA stability to produce the DNA sequence as shown in SEQ ID NO:1.

This DNA was chemically synthesized (Blue Heron, Inc,) and inserted into the NdeI and BamH1 sites of E. coli expression vector pET22b(+) (Novagen; Madison, Wis.) in order to produce cytosolic protein. This construct produces delta-plasminogen with an additional, non-native N-terminal methionine. (pET-22b(+)=pET Expression System 22b (Cat. No. 70765), EMD Biosciences, Inc., Novagen Brand, Madison, Wis.; see http://www.emdbiosciences.com product information section regarding pET-22b for details regarding vector).

Delta-Plasminogen Expression and Purification

The DNA encoding delta-plasminogen sequence was transformed into a variety of cells, and protein over-expression following induction by 1 mM IPTG (isopropyl-beta-D-thiogalactopyranoside) was analyzed by SDS-PAGE. Cell type BL21(DE3) RIL (Stratagene, La Jolla, Calif.) cells, engineered to express rare E. coli tRNAs coding for Arg, Ile, and Leu, were used for production of delta-plasminogen.

Production of delta-plasminogen was confirmed in larger scale expression in which cells were lysed and both soluble protein and purified inclusion bodies were examined by SDS-PAGE. BL21(DE3) RIL cells produced significant delta-plasminogen protein in the form of inclusion bodies. Expression estimates were 50-80 mg/L cell culture.

The following typical protocol has been used for expression of delta-plasminogen:

A single colony of BL21(DE3) RIL cells containing the delta-plasminogen vector was used to inoculate 5 ml of LB/ampicillin (100 µg/ml)/chloraniphenicol (50 µg/ml) and was incubated for 8 hours at 37° C. on a shaker. After that, a 50 µl-aliquot was taken form the cultured bacterial suspension for further growth in fresh media. The procedure was repeated after 16 hours with 6 ml of bacterial culture and 250 ml of the media. Cultures were grown at 37° C. with shaking to an OD600 nm of ~1.0, and IPTG was added to 1 mM final concentration. Cultures were grown for an additional 5 hours. Cells were harvested by centrifugation at 5,000×g and cell pellets were dissolved in 20 mM Tris pH 8.0 containing 20 mM EDTA and frozen at −80° C.

To purify delta-plasminogen, cell pellets were thawed and buffer added until the solution volume was approximately ¹⁄₂₀th that of the original cell culture volume. After that, lysozyme was added to a final concentration of 0.5 mg/ml and the cells were stirred rapidly at 4° C. for 10-15 minute. Then, Triton X-100 was added to 1% final concentration and stirring continued for another 10 min. DNAse I (0.05 mg/ml) and $MgCl_2$ (2.5 mM) were added and stirring was continued at 4° C. for 30 minutes or until the solution was no longer viscous. The final solution was centrifuged at 4° C. for 30 min at 15,000×g and the supernatant was discarded.

The cell pellet was washed three times with wash solution (50 mM Tris-HCl, pH 7.4 containing 10 mM EDTA, 1% Triton-X-100, and 0.5 M urea), and the final pellet was dissolved in 40 ml of extraction buffer (PBS, pH 7.4 containing 10 mM EDTA, 20 mM DTT, and 6 M guanidine-HCl) and stored at 4° C. overnight. After 16 hours, the solution was centrifuged for 30 minutes at 15,000×g to remove solids and the supernatant was slowly added to the refolding solution (50 mM Tris-HCl, pH 8.3, 3.5 M guanidine HCl, 0.5 M arginine HCl, 10 mM EDTA, 3 mM GSH, 0.3 mM GSSG) while stirring at 4° C. The refolding procedure was carried out at protein concentration of 0.03 mg/ml or less.

The refolding solution was kept for 2 days at 4° C. undisturbed and then dialyzed against an 8-fold volume of 0.1 M Tris-HCl pH 8.0 containing 10 mM EDTA, 0.15 M NaCl, 0.15 M arginine-HCl, over a period of 8-10 hours with frequent changes of the buffer solution.

The protein solution was then removed from dialysis and concentrated using AMICON filters with the membrane cut-off of 10 kDa to approximately 10-20 ml and dialyzed overnight versus a 100-fold volume of 0.1 M Tris pH 8.0 containing 10 mM EDTA, 0.15 M NaCl. This material was centrifuged to remove particulates, then passed over lysine affinity resin (Lysine-SEPHAROSE 4B; Amersham Biosciences, Piscataway, N.J.). Delta-plasminogen was eluted from the resin using Tris-buffered saline, pH 8.0 containing 0.2 M epsilon aminocaproic acid (εACA).

Typically, 80 mg of inclusion bodies could be isolated from 1 liter of cell culture and 40 mg could be eluted in the lysine-SEPHAROSE chromatography step.

Properties of Delta-Plasminogen

Purified delta-plasminogen appeared as a single band in the 35-40 kDa region by SDS-PAGE analysis of reduced (dithiothreitol-treated) and non-reduced protein (See FIG. 5). Its exact molecular mass, determined by MALDI mass-spectrometry, was 37,089 Da, very close to the expected value of 37,198 Da.

Figure 6:
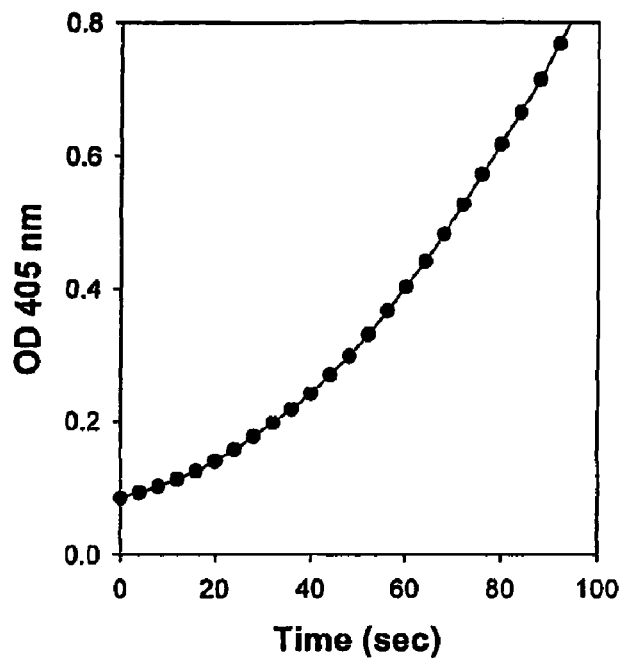
FIG. 6 is a graphic representation of activation of delta-plasminogen by urokinase. Urokinase (5.8 nM) was added to a solution of 5 μM delta-plasminogen in PBS containing 1.0 mM S-2251 at 37° C. Increases in absorbance were monitored at 405 nm.

To test whether delta-plasminogen (ΔPg) could be activated into delta-plasmin, delta-plasminogen was incubated with urokinase (1:1000 molar ratio), and the increase in serine protease activity was monitored by measuring the increase in the rate of S-2251 hydrolysis (S-2251=D-Val-Leu-Lys-p-nitroanilide, DiaPharma Group, Inc., West Chester, Ohio). As seen in FIG. 6, a parabolic increase in activity typical for the coupled reaction of activation (zymogen is converted into active enzyme (1); and enzyme cleaves the chromogenic substrate (2)) is observed. Activation of delta-plasminogen to delta-plasmin was complete within 3 minutes under these conditions. Very similar results were obtained with tPA and streptokinase.

The kinetics for the urokinase activation of delta-plasminogen were compared to those for full-length plasminogen using the method of Wohl et al. (Wohl, R. C., Summaria, L., Arzadon, L., and Robbins, K. C.; J. Biol. Chem. 253: 1402-1407 (1978), fully incorporated by reference). For this purpose, 5.8 nM urokinase was added to solutions containing various concentrations of plasmin species in the presence of 1 mM S-2251 substrate at 37° C., pH 7.5. The increase in absorbance at 405 nm was monitored and the accelerating rate of S-2251 product formation was calculated using a parabolic equation where rate=$k \cdot t^2$. Data were fit to a Michaelis-Menten kinetic model using Lineweaver-Burk analysis, resulting in the values below:

TABLE 1

Kinetics for the urokinase activation of delta-plasminogen.

| Species: | $K_m$ (µM) | $k_{cat}$ (min$^{-1}$) | $k_{cat}/K_m$ (µM$^{-1}$min$^{-1}$) |
|---|---|---|---|
| Delta-plasminogen | 30 +/− 5 | 80 +/− 10 | 2.67 |
| Plasminogen | 1.2 +/− 0.1 | 2.3 +/− 0.3 | 1.92 |

Full-length plasminogen was activated well by urokinase, with Km values similar to those found in the literature (1.7 µM; Wohl, R. C., Summaria, L., and Robbins, K. C.; J. Biol. Chem. 255(5): 2005-2013 (1980)) and equivalent kcat values.

Km values for urokinase activation of delta-plasminogen were approximately 30-fold higher than for plasminogen, possibly indicating a lower affinity of urokinase for this mutant of plasminogen. At the same time, the $k_{cat}$ value for activation of delta-plasminogen was much higher than for plasminogen: In spite of the above-mentioned differences in the $k_{cat}$ and $K_m$, their ratio, or catalytic efficiency, is approximately the same for activation of the natural and recombinantly-modified plasminogen species by urokinase. Thus, these data indicate that the presence of a "foreign" kringle 1 does not considerably affect the activation properties of the serine protease domain in delta-plasminogen.

In yet another activation experiment, delta-plasminogen was incubated with streptokinase, tPA, and urokinase and analyzed on reduced SDS-PAGE to observe the conversion of the one-chain delta-plasminogen molecule in two-chain delta-plasmin (See FIG. 5, Lanes 3-5). In all three cases, two chains (~12 kDa kringle 1 and the ~25 kDa serine protease chain) of delta-plasmin could be seen, suggesting that delta-plasminogen indeed can be activated by all three plasminogen activators.

Figure 7:
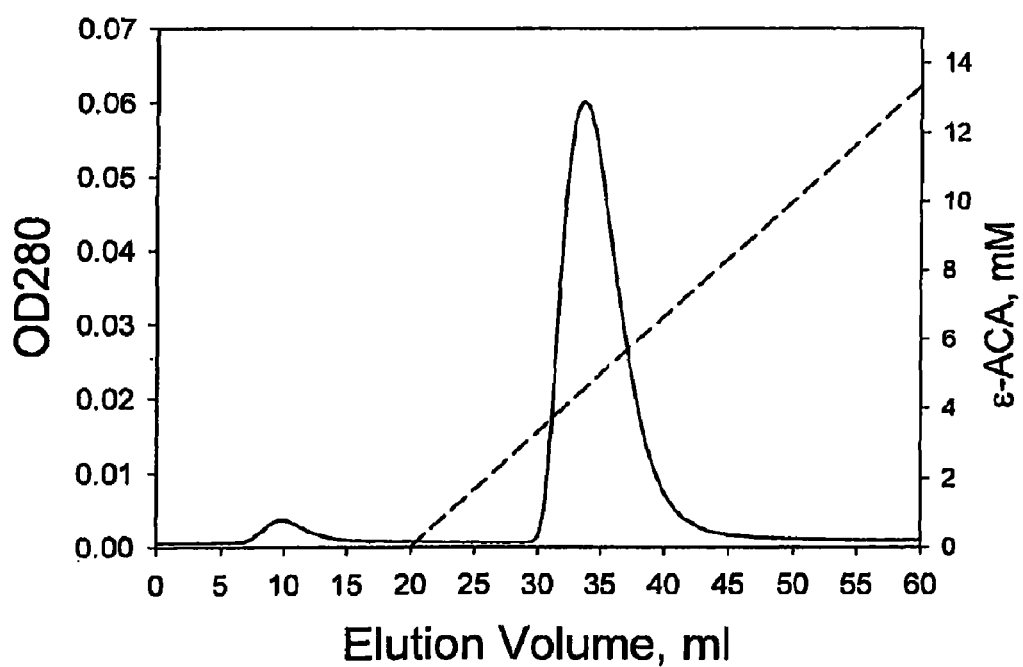
FIG. 7 is a chromatogram showing binding of delta-plasminogen to lysine-SEPHAROSE 4B: 0.5 mg of purified Delta-plasminogen was applied on the lysine-SEPHAROSE 4B column (1×3 cm) equilibrated with Tris-buffered saline, pH 7.4. Bound protein was eluted from the column by a 0-20 mM gradient of s-aminocaproic acid (ε-ACA) as a single peak. The absorbance at 280 nm and the concentration of ε-ACA, as a function of the effluent volume are presented on the graph.

As expected, delta-plasminogen bound to lysine-SEPHAROSE via kringle 1 and could be eluted from the column by the gradient of εACA as a single peak (See FIG. 7). The ability of refolded delta-plasminogen to bind lysine-SEPHAROSE indicates that the kringle domain of the molecule is properly folded and the lysine-binding site is fully active.

To further confirm the functionality of kringle 1, the binding of εACA to delta-plasminogen was measured by monitoring the associated changes in protein fluorescence as described by Matsuka et al. (Matsuka, Y. V., Novokhatny, V. V., and Kudinov, S. A., *Eur. J. Biochem.* 190:93-97 (1990)) and Douglas et al. (Douglas, J. T., von Haller, P. D., Gehrmann, M., Llinas, M., and Schaller. J., *Biochemistry* 41:3302-3310 (2002), all incorporated herein by reference). Binding of εACA to kringle 1 of delta-plasminogen results in a decrease in fluorescence, likely due to quenching of the tryptophan residues which are part of the lysine-binding site.

To monitor this process, 4 μl to 16 μl aliquots of a concentrated solution of εACA were added to 2 ml of 5 μM delta-plasminogen in 50 mM Tris buffer containing 20 mM NaCl, pH 8.0, 25° C. The fluorescence was monitored at an excitation wavelength of 298 nm and an emission wavelength of 340 nm in a FLUOROMAX fluorescence spectrophotometer (JobinYvon, Inc., Edison, N.J.); after each addition of εACA, the solution was allowed to equilibrate until no further changes in fluorescence were observed.

The resulting fluorescence values were corrected for dilution and plotted versus the concentration of εACA over a range of 0-50 μM εACA. Data were fitted by non-linear regression to obtain a $K_d$ of 11.1+/−2.3 μM, in good agreement with literature values for kringle 1 affinity for εACA of 3.2 μM (Matsuka, et al.) and 13 μM (Douglas, et al.).

One property of plasmin is its ability to bind fibrin. In order to determine whether delta-plasminogen retains the ability to interact with fibrin, its fibrin-binding properties were tested in a microtiter plate assay in which binding of delta-plasminogen to fibrin was assessed by its subsequent activation by tPA and resulting clot lysis. For this purpose, 100 μA of 5 mg/ml fibrinogen was polymerized with thrombin in each well of a microtiter plate. Various concentrations of delta-plasminogen were added on top of the fibrin clots and incubated for 1 hour at 37° C. The plate was washed extensively with PBS while the fibrin clots were still intact and attached to the wells. After washing, a 0.1-mg/ml solution of tPA was added to each well and the plate was incubated 2 hours at 37° C. As a result, some of the clots were completely dissolved and some were partially dissolved, while wells with very low amounts of delta-plasminogen and control wells remained practically intact. The degree of fibrinolysis was monitored by measuring the 280 nm absorbance of remainders of the initial clots reconstituted in 1M NaOH. The absorbance values were plotted as a function of delta-plasminogen concentration.

Figure 8:
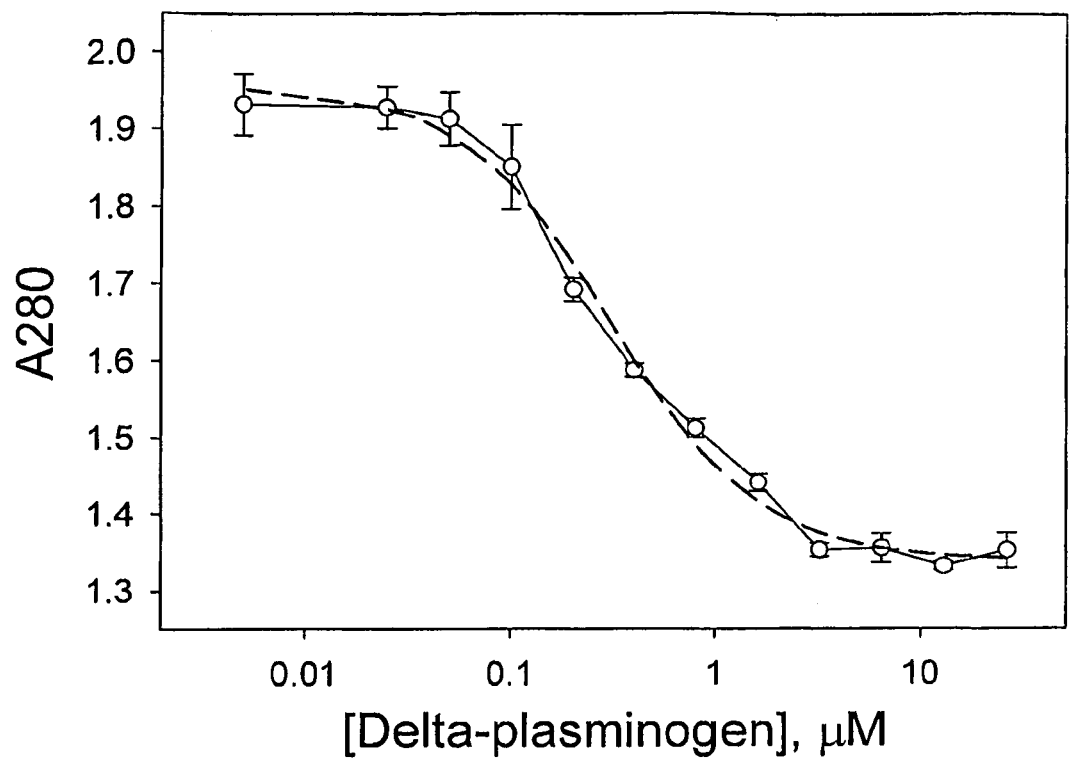
FIG. 8 shows binding of delta-plasminogen to fibrin. Varying concentrations of delta-plasminogen were incubated with fibrin clots in a microtiter plate for 1 hour at 37° C. After incubation the clots were washed extensively with PBS and a 0.1 mg/ml solution of tPA was added to each well. After a 2-hour incubation at 37° C. the liquid was removed and remaining solid clots were reconstituted with 100 μA of 1M NaOH. The amount of remaining fibrin was quantified by measuring the 280 nm absorbance of these reconstituted clots. The degree of fibrinolysis, which is a result of delta-plasminogen binding to fibrin, was plotted on the graph as a function of delta-plasminogen concentration (solid line). The dash line represents the best fit of experimental data to a binding equation.

As seen in FIG. 8, the binding of delta-plasminogen to fibrin follows a classic, sigmoidal binding curve. Using this assay, it was found that delta-plasminogen binds fibrin with affinity comparable to that of full-length plasminogen and the $C_{50}$ of this interaction (~0.2 μM) is comparable to the $K_d$ of fibrin-binding of full-length plasminogen (Lucas, M. A., Fretto, L. J., and McKee, P. A.; *J. Biol. Chem.* 258(7): 4249-4256 (1983)). These experiments indicate that delta-plasminogen can bind fibrin.

Thus, the interaction of delta-plasminogen with lysine-SEPHAROSE, its ability to bind εACA with the expected $K_d$, its ability to bind fibrin, its ability to be activated by all major plasminogen activators, and the potency of delta-plasmin toward the chromogenic plasmin substrate S-2251 all indicated that this molecule was produced in the *E. coli* system in a fully functional form.

Delta-Plasmin Purification and Formulation

Delta-plasminogen, dialyzed against 0.1M Tris buffer, pH 8.0 containing 10 mM EDTA and 0.15 M NaCl, was activated to delta-plasmin using urokinase immobilized on SEPHAROSE 4B essentially as described previously for plasmin (Marder, V. J., et al., *Thromb Haemost.*, 86(3):739-45 (2001), incorporated by reference). Activation occurred at room temperature and was monitored in real time by the increase in S-2251 activity. Depending on the amount of delta-plasminogen, which varied from batch to batch (typically 1-2 mg/ml), incubation time was 30-60 min. Upon completion of activation, when the S-2251 activity reached a plateau, urokinase-SEPHAROSE was filtered out and active delta-plasmin was captured on benzamidine-SEPHAROSE (Pharmacia). Delta-plasmin was eluted from the resin using low-pH buffer (0.2 M glycine, pH 3.0, 0.3 M NaCl, 0.2M εACA).

Figure 9:
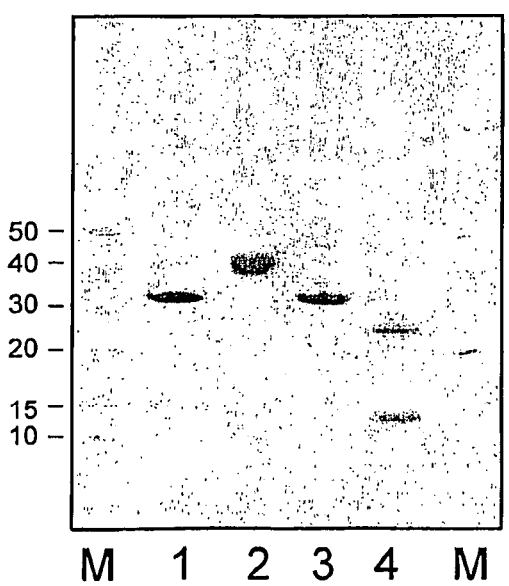
FIG. 9 shows a 8-25% gradient SDS-PAGE of starting delta-plasminogen under non-reduced (Lane 1) and reduced conditions (Lane 2) and final delta-plasmin preparation, also under non-reduced (Lane 3) and reduced (Lane 4) conditions.

The protein concentrations and S-2251 activity in elution fractions were measured. High specific activity fractions were pooled and dialyzed against multiple changes of 0.15 M NaCl, pH 3.6 at 4° C. SDS-PAGE analysis of non-reduced delta-plasmin samples (see FIG. 9, Lane 3) shows that the purity of this material is usually more than 95%. Under reduced conditions (FIG. 9, Lane 4), besides the serine protease and the kringle chains, there are two faint bands above and below the kringle band. These bands represent auto-degradation products of the serine protease domain which result from internal cleavages of its polypeptide chain; they are normally held together by disulfide bonds but become visible with PAGE under reducing conditions. The amount of auto-degradation products, which typically did not exceed 10%, was greatly reduced by conducting the benzamidine-SEPHAROSE purification step in batch mode instead of the column format.

Because delta-plasmin, similar to full-length plasmin, is prone to auto-degradation at physiological pH, pH 3.6 was chosen for the final formulation (acidified with acetic acid-saline). As shown previously for plasmin (Novokhatny, V. et al., *J Thromb Haemost.*, 1(5):1034-41 (2003), incorporated by reference) and confirmed in experiments with delta-plasmin, this low buffering-capacity, low pH formulation not only allows safe storage of active plasmins for prolonged periods of time, but is also compatible with parenteral administration of these direct thrombolytics. When mixed with plasma or neutral pH buffers, delta-plasmin is quickly re-activated.

Enzymatic Properties of Delta-Plasmin

The amidolytic activity of delta-plasmin was examined using the plasmin to substrate D-Val-Leu-Lys-p-nitroanilide (S-2251) (DiaPharma, West Chester, Ohio). At pH 7.4, 25° C.

in PBS buffer, the Michaelis-Menten constant (Kin) for S-2251 was found to be 138 M (Table 2). The kcat for the preparation was found to be 510 min$^{-1}$. Using 4-nitrophenyl 4-guanidinobenzoate hydrochloride (pNPGB) titration (Chase, T. and E. Shaw, *Methods Enzymol.* 197:20-27 (1970)), the percent of functional active sites was found to be 67%. Correcting kcat for percent active sites, a kcat of 755+/−45 min$^{-1}$ was determined. This value was very close to the value determined in the same assay for full-length plasmin, 760+/−23 min−1 and for micro-plasmin (lacking all five kringles), 795+/−24 min$^{-1}$ (See FIG. 9). These data indicate that presence or absence of kringles does not affect the catalytic activity of the serine protease domain.

The rate of inhibition of delta-plasmin by α$_2$-macroglobulin was measured using the method of Anonick et al. (Anonick, P., et al., *Thrombosis Res.* 59:449-462 (1990)). The inhibition rate was found to be 7.6+/−0.6×10$^5$ M$^{-1}$s$^{-1}$ at 22° C. in PBS buffer.

The rate of inhibition of delta-plasmin by π$_2$-antiplasmin was determined to be 1.1×10$^7$ M$^{-1}$s$^{-1}$ using the method of Wiman and Collen (Wiman, B. and D. Collen, *Eur. J. Biochem.* 84:573-578 (1978)) in which plasmin and α$_2$-antiplasmin are mixed then assayed for S-2251 activity at specific time points (Table 3). This value is comparable to reported values for plasmin of 2.5×10$^7$ M$^{-1}$s$^{-1}$ (from Anonick, et al., *Thrombosis Res.* 59:449 (1990)).

The same experiments conducted with micro-plasmin revealed α$_2$-antiplasmin inhibition rates of 1.8×10$^5$ M$^{-1}$ s$^{-1}$ and 3.1×10$^5$ M$^{-1}$ s$^{-1}$ in two separate experiments. The rate of α$_2$-antiplasmin inhibition of mini-plasmin (mini-plasmin domain composition, K5-SP) was determined to be 2.4×10$^5$ M$^{-1}$ s$^{-1}$. These data are in reasonable agreement with literature values for micro- and mini-plasmin and show that inhibition of delta-plasmin by α$_2$-antiplasmin is 40-fold faster than the inhibition of either micro-plasmin or mini-plasmin. Thus, these results indicate that delta-plasmin should be rapidly inhibited by α$_2$-antiplasmin due to the presence of kringle 1 in its structure.

Overall, the data presented in this section show that the enzymatic and inhibitory properties of delta-plasmin are similar to full-length plasmin.

TABLE 2

Steady-state kinetic parameters for various plasmin species with substrate S-2251, in PBS buffer, pH 7.4, 25° C.

|  | $K_m$ | $k_{cat}$ |
|---|---|---|
| plasmin | 193 +/− 7 µM | 760 +/− 23 min$^{-1}$ |
| mini-plasmin | 160 +/− 30 µM | 770 +/− 70 min$^{-1}$ |
| micro-plasmin | 145 +/− 13 µM | 795 +/− 24 min$^{-1}$ |
| delta-plasmin | 138 +/− 5 µM | 755 +/− 45 min$^{-1}$ |

TABLE 3

Inhibition rates for various plasmin species and inhibitors were determined at 22° C. in PBS buffer, pH 7.4.

|  | α$_2$-macroglobulin | α$_2$-antiplasmin |
|---|---|---|
| plasmin | 6.5 +/− 0.5 × 10$^5$ M$^{-1}$s$^{-1}$ | 2.5 +/− 0.5 × 10$^7$ M$^{-1}$s$^{-1}$ (lit.) |
| mini-plasmin | 7.5 +/− 0.3 × 10$^5$ M$^{-1}$s$^{-1}$ | 2.4 +/− 0.5 × 10$^5$ M$^{-1}$s$^{-1}$ |
| micro-plasmin | 7.8 +/− 0.6 × 10$^5$ M$^{-1}$s$^{-1}$ | 1.8 +/− 0.2 × 10$^5$ M$^{-1}$s$^{-1}$ |
| delta-plasmin | 7.6 +/− 0.6 × 10$^5$ M$^{-1}$s$^{-1}$ | 1.1 +/− 0.1 × 10$^7$ M$^{-1}$s$^{-1}$ |

Literature values are taken from Anonick, et al., *Thrombosis Res.* 59:449 (1990). All rates were measured according to the methods published in Anonick, et al.

In Vitro Thrombolytic Efficiency

The thrombolytic efficacy of delta-plasmin was tested in an in vitro model of catheter-assisted thrombolysis (Novokhatny, V. et al., *J Thromb Haemost.*, 1(5):1034-41 (2003), incorporated by reference) using the following experimental protocol.

Fresh whole human blood was collected into 20×0.95 cm glass tubes and allowed to clot spontaneously without additives. Tubes were incubated for 20 hr at 37° C. to allow full retraction. Retracted clots were separated from serum using USA Standard testing sieves D16 with 14 mesh, and their weights were determined. Blood clots were transferred into smaller diameter glass tubes in which the retracted clots fit tightly (0.8×7 cm). The averaged weight of the clots was ~3.6 g.

Single 1-ml doses of acidified saline, plasmin, or delta-plasmin were injected into the clot using a syringe. The clots were incubated for 1 hour at 37° C. in a THELCO laboratory oven (Jouan, Inc., Winchester, Va.). After the incubation, the clots were placed again on the sieve to remove the liquefied material and the weight of the digested clots was measured. The extent of clot lysis was determined from the difference between the initial clot weight and the weight of residual clot and was expressed as a percent of clot weight reduction.

Figure 10:
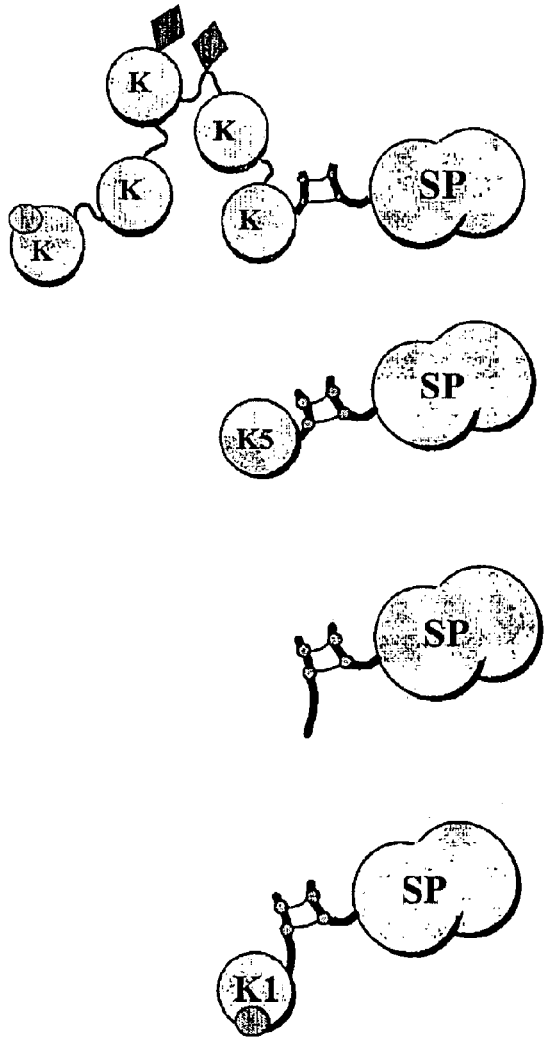
FIG. 10 shows schematic diagrams of plasmin, mini-plasmin, micro-plasmin, and delta-plasmin, along with a corresponding characterization of enzymatic activity ($k_{cat}$ and $K_M$ with respect to substrate S-2251 (D-Val-Leu-Lys-p-nitroanilide, DiaPharma Group, Inc., West Chester, Ohio)).
Figure 11:
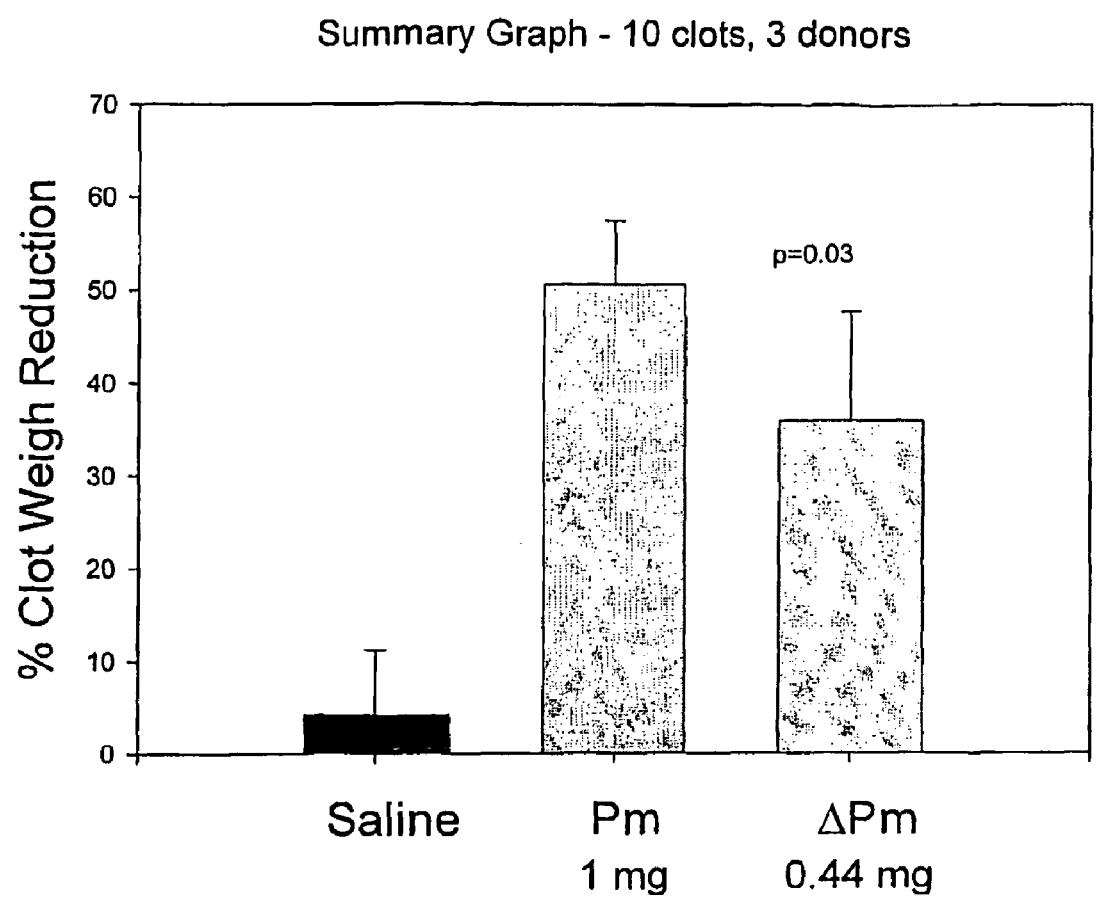
FIG. 11 is a graphic representation of delta-plasmin-induced lysis of retracted whole-blood clots. Each clot (0.8×7 cm) was injected with a 1 ml volume of vehicle (acidified saline, pH 3.6), plasmin (1.0 mg/ml), or delta-plasmin (0.44 mg/ml), and clot dissolution was allowed to proceed at 37° C. for 1 hour.

FIG. 10 shows the results of the lysis experiments with delta-plasmin in this model. The infusion of single 0.44 mg (equivalent to 1 mg/ml of plasmin on a molar to basis) dose of delta-plasmin resulted in 36% clot weight reduction within 60 min. At the same time, the weight of the clots infused with saline decreased only by 4%. Plasmin (1.0 mg) resulted in 50% clot weight reduction in the same period. Thus, these data show that delta-plasmin exhibits thrombolytic potency and can be used as a direct thrombolytic agent.

What is claimed is:

1. A polynucleotide comprising a nucleotide sequence encoding a polypeptide having a single N-terminal kringle domain which is at least 90% identical to the kringle 1 domain of native human plasminogen; directly attached to a C-terminal domain which is at least 90% identical to the activation site and serine protease domain of native human plasminogen, wherein the polypeptide binds to immobilized lysine and can be activated by a plasminogen activator.

2. The polynucleotide of claim 1, wherein the encoded polypeptide is SEQ ID NO: 2 with no more than 30 amino acid substitutions.

3. The polynucleotide of claim 1, wherein the encoded polypeptide is at least 90% identical to the sequence shown in SEQ ID NO: 2.

4. The polynucleotide of claim 1, wherein the encoded polypeptide is at least 95% identical to the sequence shown in SEQ ID NO: 2.

5. The polynucleotide of claim 1, wherein the encoded polypeptide is the sequence shown in SEQ ID NO: 2.

6. The polynucleotide of claim 1, wherein the nucleotide sequence of the polynucleotide is the sequence shown in SEQ ID NO: 1 or a degenerate variant that encodes SEQ ID NO: 2.

7. The polynucleotide of claim 1, wherein the polypeptide exhibits a fibrinolytic activity that is inhibited by α2-antiplasmin at a rate of inhibition that is at least about 5-fold faster than the rate of inhibition of the fibrinolytic activity of mini-plasmin by α2-antiplasmin.

8. An expression vector comprising the polynucleotide of claim 1.

9. A cultured cell comprising the expression vector of claim 8.

10. The polynucleotide of claim 1, wherein the encoded polypeptide is at least 98% identical to the sequence shown in SEQ ID NO: 2.

* * * * *

SEQUENCE LISTING

<160> NUMBER OF SEQ ID NOS: 9

<210> SEQ ID NO 1
<211> LENGTH: 1008
<212> TYPE: DNA
<213> ORGANISM: Artificial Sequence
<220> FEATURE:
<223> OTHER INFORMATION: polynucleotide comprising a nucleotide sequence
      encoding a polypeptide having a single N-terminal kringle domain
      homologous to a kringle domain of native human plasminogen

<400> SEQUENCE: 1

```
aaagtctatt tatctgaatg taaaacaggc aatggtaaaa actatcgcgg taccatgtcc      60
aaaacaaaaa acggtatcac ttgtcaaaaa tggtctagca cttcaccca tcgtcctcgt     120
ttctcccctg cgacccatcc ctctgaaggc ctcgaagaaa actactgccg caaccccgat    180
aatgatcctc aaggcccatg tgttatact accgatcctg aaaaacgtta tgactattgc     240
gatatcttag aatgcgcagc cccttctttt gattgcggca accacaagt tgaacccaag     300
aaatgtccag tcgtgttgt cggcggttgt gttgcgcatc cccacagttg gccgtggcag    360
gtctcattac gtacccggtt tggaatgcac ttttgtggcg gcactctcat ctcgcccgaa    420
tgggttctta cagctgcaca ctgtttggaa aaaagcccc gtccttcttc ttataaagtt     480
atcctcggcg cacatcaaga agtcaattta gaacctcatg tacaagaaat cgaagtatct    540
cgtttattcc tggaaccgac tcgcaaagac atcgcattac ttaaactgtc ctcccccgct    600
gtgatcaccg ataaagtaat tcccgcgtgt ttaccttctc ctaattatgt tgttgcagat    660
cgtacagaat gctttattac cggctggggt gaaactcaag gtactttttgg tgcgggactc   720
ctgaaagaag cacagttacc agtcatcgaa acaaagtat gtaatcgcta cgaattctta     780
aacggtcgtg ttcaatccac agaattgtgc gcaggtcatt tagcaggtgg cactgatagc    840
tgtcaaggtg attcaggtgg tcctctcgta tgtttcgaaa aagataaata tattctgcaa    900
ggcgtcacct cttggggttt aggttgtgct cgtcccaata aacctggtgt atatgtacgt    960
gtaagtcgtt ttgttacctg gattgaaggt gttatgcgga caaactaa                1008
```

<210> SEQ ID NO 2
<211> LENGTH: 335
<212> TYPE: PRT
<213> ORGANISM: Artificial Sequence
<220> FEATURE:
<223> OTHER INFORMATION: a polypeptide having a single N-terminal kringle domain homologous to a kringle domain of native human plasminogen

<400> SEQUENCE: 2

```
Lys Val Tyr Leu Ser Glu Cys Lys Thr Gly Asn Gly Lys Asn Tyr Arg
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Ala Ala Pro Ser Phe Asp Cys Gly Lys Pro Gln
                85                  90                  95

Val Glu Pro Lys Lys Cys Pro Gly Arg Val Val Gly Gly Cys Val Ala
            100                 105                 110

His Pro His Ser Trp Pro Trp Gln Val Ser Leu Arg Thr Arg Phe Gly
        115                 120                 125

Met His Phe Cys Gly Gly Thr Leu Ile Ser Pro Glu Trp Val Leu Thr
    130                 135                 140

Ala Ala His Cys Leu Glu Lys Ser Pro Arg Pro Ser Ser Tyr Lys Val
145                 150                 155                 160

Ile Leu Gly Ala His Gln Glu Val Asn Leu Glu Pro His Val Gln Glu
```

```
                     165                 170                 175
Ile Glu Val Ser Arg Leu Phe Leu Glu Pro Thr Arg Lys Asp Ile Ala
            180                 185                 190
Leu Leu Lys Leu Ser Ser Pro Ala Val Ile Thr Asp Lys Val Ile Pro
            195                 200                 205
Ala Cys Leu Pro Ser Pro Asn Tyr Val Val Ala Asp Arg Thr Glu Cys
            210                 215                 220
Phe Ile Thr Gly Trp Gly Glu Thr Gln Gly Thr Phe Gly Ala Gly Leu
225                 230                 235                 240
Leu Lys Glu Ala Gln Leu Pro Val Ile Glu Asn Lys Val Cys Asn Arg
            245                 250                 255
Tyr Glu Phe Leu Asn Gly Arg Val Gln Ser Thr Glu Leu Cys Ala Gly
            260                 265                 270
His Leu Ala Gly Gly Thr Asp Ser Cys Gln Gly Asp Ser Gly Gly Pro
            275                 280                 285
Leu Val Cys Phe Glu Lys Asp Lys Tyr Ile Leu Gln Gly Val Thr Ser
            290                 295                 300
Trp Gly Leu Gly Cys Ala Arg Pro Asn Lys Pro Gly Val Tyr Val Arg
305                 310                 315                 320
Val Ser Arg Phe Val Thr Trp Ile Glu Gly Val Met Arg Asn Asn
            325                 330                 335

<210> SEQ ID NO 3
<211> LENGTH: 2432
<212> TYPE: DNA
<213> ORGANISM: Homo sapiens
<220> FEATURE:
<221> NAME/KEY: misc_feature
<222> LOCATION: (1)..(2432)
<223> OTHER INFORMATION: Human plasminogen

<400> SEQUENCE: 3
atggaacata aggaagtggt tcttctactt cttttatttc tgaaatcagg tcaaggagag      60
cctctggatg actatgtgaa tacccagggg gcttcactgt tcagtgtcac taagaagcag     120
ctgggagcag gaagtataga agaatgtgca gcaaaatgtg aggaggacga agaattcacc     180
tgcagggcat tccaatatca cagtaaagag caacaatgtg tgataatggc tgaaaacagg     240
aagtcctcca taatcattag gatgagagat gtagttttat ttgaaaagaa agtgtatctc     300
tcagagtgca agactgggaa tggaaagaac tacagaggga cgatgtccaa aacaaaaaat     360
ggcatcacct gtcaaaaatg gagttccact tctccccaca gacctagatt ctcacctgct     420
acacacccct cagagggact ggaggagaac tactgcagga atccagacaa cgatccgcag     480
gggccctggt gctatactac tgatccagaa aagagatatg actactgcga cattcttgag     540
tgtgaagagg aatgtatgca ttgcagtgga gaaaactatg acggcaaaat ttccaagacc     600
atgtctggac tggaatgcca ggcctggact ctcagagcc cacacgctca tggatacatt     660
ccttccaaat ttccaaacaa gaacctgaag aagaattact gtcgtaaccc cgataggggag     720 ctgcggcctt ggtgtttcac caccgacccc aacaagcgct gggaactttg cgacatcccc     780
cgctgcacaa cacctccacc atcttctggt cccacctacc agtgtctgaa gggaacaggt     840
gaaaactatc gcgggaatgt ggctgttacc gtttccgggc acacctgtca gcactggagt     900
gcacagaccc ctcacacaca taacaggaca ccagaaaact ccccctgcaa aaatttggat     960
gaaaactact gccgcaatcc tgacggaaaa agggccccat ggtgccatac aaccaacagc    1020
caagtgcggt gggagtactg taagataccg tcctgtgact cctccccagt atccacggaa    1080
```

-continued

```
caattggctc ccacagcacc acctgagcta accccctgtgg tccaggactg ctaccatggt    1140
gatggacaga gctaccgagg cacatcctcc accaccacca caggaaagaa gtgtcagtct    1200
tggtcatcta tgacaccaca ccggcaccag aagacccccag aaaactaccc aaatgctggc    1260
ctgacaatga actactgcag gaatccagat gccgataaag cccctggtg ttttaccaca    1320 gaccccagcg tcaggtggga gtactgcaac ctgaaaaaat gctcaggaac agaagcgagt    1380
gttgtagcac ctccgcctgt tgtcctgctt ccagatgtag agactccttc cgaagaagac    1440
tgtatgtttg ggaatgggaa aggataccga ggcaagaggg cgaccactgt tactgggacg    1500
ccatgccagg actgggctgc ccaggagccc catagacaca gcattttcac tccagagaca    1560
aatccacggg cgggtctgga aaaaaattac tgccgtaacc ctgatggtga tgtaggtggt    1620
ccctggtgct acacgacaaa tccaagaaaa ctttacgact actgtgatgt ccctcagtgt    1680
gcggcccctt catttgattg tgggaagcct caagtggagc cgaagaaatg tcctggaagg    1740
gttgtggggg ggtgtgtggc ccacccacat tcctggccct ggcaagtcag tcttagaaca    1800
aggtttggaa tgcacttctg tggaggcacc ttgatatccc cagagtgggt gttgactgct    1860
gcccactgct tggagaagtc cccaaggcct tcatcctaca aggtcatcct gggtgcacac    1920
caagaagtga atctcgaacc gcatgttcag gaaatagaag tgtctaggct gttcttggag    1980
cccacacgaa aagatattgc cttgctaaag ctaagcagtc ctgccgtcat cactgacaaa    2040
gtaatcccag cttgtctgcc atccccaaat tatgtggtcg ctgaccggac cgaatgtttc    2100
atcactggct ggggagaaac ccaaggtact tttggagctg gccttctcaa ggaagcccag    2160
ctccctgtga ttgagaataa agtgtgcaat cgctatgagt ttctgaatgg aagagtccaa    2220
tccaccgaac tctgtgctgg gcatttggcc ggaggcactg acagttgcca gggtgacagt    2280
ggaggtcctc tggttttgctt cgagaaggac aaatacattt tacaaggagt cacttcttgg    2340
ggtcttggct gtgcacgccc caataagcct ggtgtctatg ttcgtgtttc aaggtttgtt    2400
acttggattg agggagtgat gagaaataat ta                                  2432
```

<210> SEQ ID NO 4
<211> LENGTH: 810
<212> TYPE: PRT
<213> ORGANISM: Homo sapiens
<220> FEATURE:
<221> NAME/KEY: Polypeptide
<222> LOCATION: (1)..(810)
<223> OTHER INFORMATION: Human plasminogen

<400> SEQUENCE: 4

```
Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
```

-continued

```
            115                 120                 125
Ser Thr Ser Pro His Arg Pro Arg Phe Ser Pro Ala Thr His Pro Ser
130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                    165                 170                 175
Asp Ile Leu Glu Cys Glu Glu Cys Met His Cys Ser Gly Glu Asn
                180                 185                 190
Tyr Asp Gly Lys Ile Ser Lys Thr Met Ser Gly Leu Glu Cys Gln Ala
                195                 200                 205
Trp Asp Ser Gln Ser Pro His Ala His Gly Tyr Ile Pro Ser Lys Phe
210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                    245                 250                 255
Cys Asp Ile Pro Arg Cys Thr Thr Pro Pro Ser Ser Gly Pro Thr
                260                 265                 270
Tyr Gln Cys Leu Lys Gly Thr Gly Glu Asn Tyr Arg Gly Asn Val Ala
            275                 280                 285
Val Thr Val Ser Gly His Thr Cys Gln His Trp Ser Ala Gln Thr Pro
290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                    325                 330                 335
Thr Thr Asn Ser Gln Val Arg Trp Glu Tyr Cys Lys Ile Pro Ser Cys
                340                 345                 350
Asp Ser Ser Pro Val Ser Thr Glu Gln Leu Ala Pro Thr Ala Pro Pro
            355                 360                 365
Glu Leu Thr Pro Val Val Gln Asp Cys Tyr His Gly Asp Gly Gln Ser
370                 375                 380
Tyr Arg Gly Thr Ser Ser Thr Thr Thr Gly Lys Lys Cys Gln Ser
385                 390                 395                 400
Trp Ser Ser Met Thr Pro His Arg His Gln Lys Thr Pro Glu Asn Tyr
                    405                 410                 415
Pro Asn Ala Gly Leu Thr Met Asn Tyr Cys Arg Asn Pro Asp Ala Asp
                420                 425                 430
Lys Gly Pro Trp Cys Phe Thr Thr Asp Pro Ser Val Arg Trp Glu Tyr
            435                 440                 445
Cys Asn Leu Lys Lys Cys Ser Gly Thr Glu Ala Ser Val Val Ala Pro
450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                    485                 490                 495
Val Thr Gly Thr Pro Cys Gln Asp Trp Ala Ala Gln Glu Pro His Arg
                500                 505                 510
His Ser Ile Phe Thr Pro Glu Thr Asn Pro Arg Ala Gly Leu Glu Lys
            515                 520                 525
Asn Tyr Cys Arg Asn Pro Asp Gly Asp Val Gly Gly Pro Trp Cys Tyr
530                 535                 540
```

```
Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
                660                 665                 670

Ser Pro Ala Val Ile Thr Asp Lys Val Ile Pro Ala Cys Leu Pro Ser
            675                 680                 685

Pro Asn Tyr Val Val Ala Asp Arg Thr Glu Cys Phe Ile Thr Gly Trp
690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
                740                 745                 750

Thr Asp Ser Cys Gln Gly Asp Ser Gly Gly Pro Leu Val Cys Phe Glu
            755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 5
<211> LENGTH: 79
<212> TYPE: PRT
<213> ORGANISM: Artificial Sequence
<220> FEATURE:
<223> OTHER INFORMATION: kringle domain 1 of native human plasmin(ogen)

<400> SEQUENCE: 5

Cys Lys Thr Gly Asn Gly Lys Asn Tyr Arg Gly Thr Met Ser Lys Thr
1               5                   10                  15

Lys Asn Gly Ile Thr Cys Gln Lys Trp Ser Ser Thr Ser Pro His Arg
            20                  25                  30

Pro Arg Phe Ser Pro Ala Thr His Pro Ser Glu Gly Leu Glu Glu Asn
        35                  40                  45

Tyr Cys Arg Asn Pro Asp Asn Asp Pro Gln Gly Pro Trp Cys Tyr Thr
    50                  55                  60

Thr Asp Pro Glu Lys Arg Tyr Asp Tyr Cys Asp Ile Leu Glu Cys
65                  70                  75

<210> SEQ ID NO 6
<211> LENGTH: 78
<212> TYPE: PRT
```

```
<213> ORGANISM: Artificial Sequence
<220> FEATURE:
<223> OTHER INFORMATION: kringle domain 2 of native human plasmin(ogen)

<400> SEQUENCE: 6

Cys Met His Cys Ser Gly Glu Asn Tyr Asp Gly Lys Ile Ser Lys Thr
1               5                   10                  15

Met Ser Gly Leu Glu Cys Gln Ala Trp Asp Ser Gln Ser Pro His Ala
            20                  25                  30

His Gly Tyr Ile Pro Ser Lys Phe Pro Asn Lys Asn Leu Lys Lys Asn
        35                  40                  45

Tyr Cys Arg Asn Pro Asp Arg Glu Leu Arg Pro Trp Cys Phe Thr Thr
    50                  55                  60

Asp Pro Asn Lys Arg Trp Glu Leu Cys Asp Ile Pro Arg Cys
65                  70                  75

<210> SEQ ID NO 7
<211> LENGTH: 78
<212> TYPE: PRT
<213> ORGANISM: Artificial Sequence
<220> FEATURE:
<223> OTHER INFORMATION: kringle domain 3 of native human plasmin(ogen)

<400> SEQUENCE: 7

Cys Leu Lys Gly Thr Gly Glu Asn Tyr Arg Gly Asn Val Ala Val Thr
1               5                   10                  15

Val Ser Gly His Thr Cys Gln His Trp Ser Ala Gln Thr Pro His Thr
            20                  25                  30

His Asn Arg Thr Pro Glu Asn Phe Pro Cys Lys Asn Leu Asp Glu Asn
        35                  40                  45

Tyr Cys Arg Asn Pro Asp Gly Lys Arg Ala Pro Trp Cys His Thr Thr
    50                  55                  60

Asn Ser Gln Val Arg Trp Glu Tyr Cys Lys Ile Pro Ser Cys
65                  70                  75

<210> SEQ ID NO 8
<211> LENGTH: 78
<212> TYPE: PRT
<213> ORGANISM: Artificial Sequence
<220> FEATURE:
<223> OTHER INFORMATION: kringle domain 4 of native human plasmin(ogen)

<400> SEQUENCE: 8

Cys Tyr His Gly Asp Gly Gln Ser Tyr Arg Gly Thr Ser Ser Thr Thr
1               5                   10                  15

Thr Thr Gly Lys Lys Cys Gln Ser Trp Ser Ser Met Thr Pro His Arg
            20                  25                  30

His Gln Lys Thr Pro Glu Asn Tyr Pro Asn Ala Gly Leu Thr Met Asn
        35                  40                  45

Tyr Cys Arg Asn Pro Asp Ala Asp Lys Gly Pro Trp Cys Phe Thr Thr
    50                  55                  60

Asp Pro Ser Val Arg Trp Glu Tyr Cys Asn Leu Lys Lys Cys
65                  70                  75

<210> SEQ ID NO 9
<211> LENGTH: 80
<212> TYPE: PRT
<213> ORGANISM: Artificial Sequence
<220> FEATURE:
<223> OTHER INFORMATION: kringle domain 5 of native human plasmin(ogen)

<400> SEQUENCE: 9
```

-continued

```
Cys Met Phe Gly Asn Gly Lys Gly Tyr Arg Gly Lys Arg Ala Thr Thr
1               5                   10                  15

Val Thr Gly Thr Pro Cys Gln Asp Trp Ala Ala Gln Glu Pro His Arg
            20                  25                  30

His Ser Ile Phe Thr Pro Glu Thr Asn Pro Arg Ala Gly Leu Glu Lys
            35                  40                  45

Asn Tyr Cys Arg Asn Pro Asp Gly Asp Val Gly Gly Pro Trp Cys Tyr
        50                  55                  60

Thr Thr Asn Pro Arg Lys Leu Tyr Asp Tyr Cys Asp Val Pro Gln Cys
65                  70                  75                  80
```